(12) United States Patent
Marshall (10) Patent No.: US 7,678,557 B2
(45) Date of Patent: Mar. 16, 2010

(54) METHODS FOR THE ACCUMULATION AND RETENTION OF IMMUNE-ENHANCING, BACTERIAL-DERIVED RIBONUCLEOTIDES (ORN) IN BACTERIA

(76) Inventor: William E. Marshall, 155 1st Avenue S., Naples, FL (US) 34102-5946

( * ) Notice: Subject to any disclaimer, the term of this patent is extended or adjusted under 35 U.S.C. 154(b) by 444 days.

(21) Appl. No.: 11/284,517

(22) Filed: Nov. 22, 2005

(65) Prior Publication Data
US 2006/0147465 A1 Jul. 6, 2006

Related U.S. Application Data

(63) Continuation-in-part of application No. 10/800,926, filed on Mar. 15, 2004, now Pat. No. 7,189,834, which is a continuation-in-part of application No. 09/883,550, filed on Jun. 18, 2001, now abandoned, which is a continuation of application No. 09/193,653, filed on Nov. 17, 1998, now abandoned, which is a continuation-in-part of application No. 08/739,264, filed on Oct. 29, 1996, now Pat. No. 5,840,318, which is a continuation-in-part of application No. 08/517,016, filed on Aug. 18, 1995, now abandoned, which is a continuation-in-part of application No. 08/376,175, filed on Jan. 20, 1995, now abandoned, which is a continuation-in-part of application No. 08/059,745, filed on May 11, 1993, now abandoned.

(51) Int. Cl.
*C12P 1/04* (2006.01)
*C12P 1/00* (2006.01)
*C07H 21/04* (2006.01)

(52) U.S. Cl. .................. 435/170; 435/41; 536/23.1
(58) Field of Classification Search .................. None
See application file for complete search history.

(56) References Cited

U.S. PATENT DOCUMENTS

| 4,243,687 A | * | 1/1981 | Kline | 426/62 |
| 4,285,931 A | * | 8/1981 | Limjuco et al. | 424/241.1 |
| 6,322,994 B1 | * | 11/2001 | Reid | 435/29 |
| 6,471,966 B1 | * | 10/2002 | Pelaez et al. | 424/242.1 |

FOREIGN PATENT DOCUMENTS

EP 154614 A2 * 9/1985

OTHER PUBLICATIONS

Fruton et al., General Biochemistry, John Wiley and Sons, Inc. 1954, pp. 71-72, 185.
Sanders, Mary Ellen, "Probiotics: Considerations for Human Health", Nutrition Reviews, Mar. 2003, pp. 91-99, vol. 61 No. 3.
Shanahan, Fergus, "Probiotics and the Immune Response: How Much Can We Expect?", Journal of Pediatric Gastroenteroloty and Nutrition, Jun. 2004, pp. S748-S749, vol. 39, Suppl 3, 2004.
White et al., Principles of Biochemistry, McGraw-Hill, 1964, p. 170.

* cited by examiner

*Primary Examiner*—Robert A Zeman
(74) *Attorney, Agent, or Firm*—McKee, Voorhees & Sease, P.L.C.

(57) ABSTRACT

The invention relates to methods for the accumulation and retention of immune-enhancing, bacterial-derived ribonucleotides smaller than 10,000 Daltons (ORN<10 kDa) in bacteria that are produced when bacteria are grown naturally, allowing the pH of the growth medium to become acidic. The immune-enhancing, bacterial-derived ribonucleotides (ORN) and bacteria comprising ORN are useful in the preparation of animal feed or animal drinking water as well as for use in enhancing the immune system of an animal and/or its resistance to infection. The invention also discloses methods of preventing the loss of ORN during bacterial production and storage as well as methods to aid in the release of ORN when consumed by an animal.

6 Claims, 2 Drawing Sheets

METHODS FOR THE ACCUMULATION AND RETENTION OF IMMUNE-ENHANCING, BACTERIAL-DERIVED RIBONUCLEOTIDES (ORN) IN BACTERIA

CROSS REFERENCE TO RELATED APPLICATIONS

This application is a continuation-in-part that claims the benefit of priority under 35 U.S.C. § 120, to co-pending application Ser. No. 10/800,926 filed on Mar. 15, 2004, which is a continuation-in-part of Ser. No. 09/883,550 filed on Jun. 18, 2001, which is a continuation of Ser. No. 08/739,264 filed Oct. 29, 1996 now U.S. Pat. No. 5,840,318, which is a continuation-in-part of Ser. No. 08/517,016 filed Oct. 18, 1995 now abandoned, which is a continuation-in-part of Ser. No. 08/376,175 filed Jan. 20, 1995 now abandoned, which is a continuation-in-part of Ser. No. 08/059,745 filed May 11, 1993 now abandoned and is also a continuation-in-part that claims the benefit of priority under 35 U.S.C. § 120, of application Ser. No. 09/429,199 filed on Oct. 28, 1999 now U.S. Pat. No. 6,589,771 B1, the contents of which are hereby incorporated by reference in their entirety.

FIELD OF THE INVENTION

Embodiments of the invention relate generally to the field of bacterial production and probiotics and more particularly to the discovery of immune-enhancing, bacterial-derived ribonucleotides (ORN) in bacteria and methods for their accumulation and retention inside bacteria, their uses in bacterial production and storage as well as for their uses in the preparation of compositions for animal consumption and treatments.

BACKGROUND OF THE INVENTION

Microorganisms commonly encounter threatening changes in their environments. These changes include depletion of nutrients, shifts in pH, temperature and pressure, and sharing habitats with invading organisms. A commonly encountered stress of animal-associated bacteria and one of importance to a study of infectious diseases is that induced through the transfer of cultures from their propagation media into different media. This stress is especially pronounced when the bacteria are transferred to a media of neutral pH with altered or reduced levels of nutrients, such as when exogenous bacteria enter an animal or when endogenous bacteria penetrate sterile zones and tissues from their non-sterile habitats. During growth, bacteria form H+ which accumulates in both the cell and the media.

When encountering normal and naturally-occurring stresses, bacteria release products which the inventor has named stress response factors, (SRFs). These SRFs include polymers of nucleic acids and their partial and complete hydrolysates including a mixture of about a dozen oligoribonucleotides (ORN) ranging from 1-30 nucleotides, which are resistant to further hydrolysis by RNAse.

The present inventor has found that a series of mild stresses, mimicking those commonly experienced when bacterial environments change, induces the release of these oligoribonucleotides. Their release does not kill or injure the bacteria from which they were released, but rather assists them in establishing a colony in a new environment by increasing their rate of mutation and their rate of growth.

These oligoribonucleotides are released when bacteria enter the pH neutral environment of animals, such as the mouth, nose, oropharyngeal cavity, urethra and vagina.

Through co-evolution in a shared habitat, the immune systems of animals and humans have adapted a protective response to the appearance of these ORN in anticipation of a microbial invasion. This immune response to the released ORN precedes its detection of bacteria entering the pH neutral body fluids or attempting to invade horizontally onto sterile tissue, (e.g. from the nose to the sinus, from vagina to uterus). Encountering neutral pH will induce the release of these ORN, which will serve to alert the host to a potential penetration onto a sterile area or into sterile tissue. This immune response follows the stimulation of embedded sentinel cells, e.g. in oral pharyngeal tissue as well as the circulating sentry cells monocytes and macrophages, and B- and T-cells of the immune system.

Specifically, the macrophage has adapted a preemptory reaction to the presence of the oligoribonucleotides (ORN) that prepares the immune system to defend the host against infection. For example, when ingested bacteria encounter neutral pH or are overcrowded by the presence of growing pathogens, they will release readily absorbable, non-toxic ORN which activate tissue macrophages to release Interleukin-1, IL-1, Interleukin-6, IL-6, and Tumor Necrosis Factor, alpha, TNFα which stimulate other cells of the immune system. After being highly activated, exposed macrophages down-regulate the surface receptors, CD-14 and CD-16, thereby desensitizing the cell from over-activation by the subsequent interaction with bacterial toxins if infection occurs.

The present inventor has found that the oligomeric fraction having a molecular weight <10 kDa and, in particular, between 500 and 3,000 Da are readily absorbed, are non-toxic, and both activate and modulate the immune system. The products less than 10 kDa in size are non-toxic when fed or injected and contain further a group of compounds of oligomeric size, i.e. 0.5 to 3 kDa that activate and modulate macrophages. Macrophages are activated to release cytokines at levels deemed helpful to combating infections and are also down-modulated to prevent their over-activation with its subsequent release of host-threatening levels of cytokines and becoming overly cytotoxic resulting in the perforation of organs.

As sentry cells, macrophages circulate in the blood and lymph as well as reside in specialized endothelial tissues and organs. They are among the host's first lines of defense, releasing interleukin signals, destroying microbes and stimulating other immune cells to destroy diseased cells of the host. Approximately twenty different interleukins can be released modifying, amplifying, restricting and dampening messages as the system is stimulated. Thus, the macrophage's signal is key to initiating and enforcing the appropriate immune response. In an infection, bacterial endotoxin (lipopolysaccharide, LPS), binds to the TOLL-like receptor, TLR-4 and the CD-16 surface molecules on macrophages stimulating them and inducing the release of yet higher levels and combinations of IL-1, IL-6 and TNF. These signals, in turn, induce fever, fatigue, cardiovascular hypotension, renal failure and can dictate the death of the host in "septic shock".

By down-regulating the numbers of CD-14 and CD-16 receptors on the surface of the macrophage, the oligomers released by high levels of stressed bacteria help to ensure that the macrophage does not become over-activated by interleukins thereby creating a system which may go awry killing the host.

Monocytes also respond to the presence of released bacterial ORN by escaping apoptosis and maturing into macrophages.

Thirteen different species of animal-associated bacteria have been found to release oligoribonucleotides <10 kDa when stressed. However, the distribution of polymer:oligomer:monomer is not equal amongst these species. The levels of ORN accumulated and released are related to the rate of growth of the bacteria. Therefore, not all strains of bacteria, even of the same species, release levels of oligomers sufficient to protect animals against a subsequent bacterial invasion. Feral colonies of bacteria yield more oligoribonucleotides (ORN) when initially stressed than non-feral or laboratory strains. However, inducing a stress upon a laboratory strain before re-propagation will stimulate its growth rate and accumulation of ORN, comparable to that occurring when a feral strain was stressed.

The fraction >10 kDa is toxic when injected into mice, producing a ruffled fur coat, huddling and diarrhea. However, the fraction <10 kDa activates and modulates macrophages, is non-toxic when fed or injected into mice and protects them against a subsequent lethal challenge of injected endotoxin.

The present inventor has found that the ORN <10 kDa are a rich new source of natural, normally-occurring, co-evolutionarily evolved immune modulators that can be safely used to protect animals and humans from infections and the over-stimulation of their immune system. In addition, this fraction contains compounds that can be used to adjust the expression of individual surface receptors on macrophages to re-center a dysfunctional immune system.

Furthermore, in vitro and in vivo testing indicates the potential role of ORN <10 kDa as adjuvants by stimulating the production of antibodies. Human B-cells were stimulated in cell culture and mice demonstrated increased B-cell activity when an experimental vaccine against melanoma was injected with ORN<10 kDa in a trial.

An unusual feature of the ORN<10 kDa that possess immune stimulating capacity is their resistance to hydrolysis by RNase (product R-7003 purchased from Sigma Chemical Co.) when used as directed by the manufacturer (incubating 750 µL of ORNs with 50 µg of RNase at 37° C. for 3 hr). The pattern of the ORN<10 kDa on Sephadex G-10 was the same before and after RNase treatment showing no further reduction in molecular size.

The resistance of ORN<10 kDa to RNase suggests that the ORN have unusual structures. Some may have substitutions on their bases and ribose (e.g., methyl and other groups) or may have nucleotide strands held together by complementary hydrogen bonding with itself. These unusual structural conditions leading to resistance to RNase are believed to be responsible for their unique stimulation and modulation of the immune system.

Through co-habitation with bacteria, the immune system has evolved to recognize the bacterial origin of these ORN. Besides the unusual structures that prohibited further hydrolysis by RNase, the inventor believes that the immune system recognizes as "bacterial" certain base sequences in the ORN<10 kDa. Their importance to bacteria is evidenced by how well conserved they are across genera. Their ubiquity, consistency and conservation over many genera of bacteria have permitted the immune system to invest a significant response to their sudden appearance.

The <10 kDa ORN collected from heat-killed bacteria stimulate monocytes in cell culture but do not protect mice from endotoxic death. Therefore pasteurized products might be erroneously considered effective if demonstrated in a reductionistic assay similar to the one previously described. (Mangan D F, Welch G R, Wahl S M, 1991, Lipopolysaccharide, tumor necrosis factor-α, and IL-1B prevent programmed cell death (apoptosis) in human peripheral blood monocytes, J Immunol 146:1541-6).

The discovery of the release of immune-activating and modulating ORN <10 kDa has broad implications to improving the immune response through both diet and pharmaceutical preparations for humans and animals. Dairy products like milk, cheese, and yogurts contain viable bacteria, which, when transferred to the nutrient deprived environment of pH neutral body fluids, such as the mouth, release ORN. More effective health outcomes could be gained from consuming such products if they were formulated to release biologically significant amounts of ORN or by extending the dwell-time of the bacteria or ORN in the mouth and throat or by fortifying pasteurized products by adding back the viable bacteria lost during pasteurization or by the addition of ORN possessing greater stimulating powers.

Numerous patents teach the healthful benefits of administering viable bacteria to humans and animals either orally or parenterally to provide immune stimulation. Their mode of action is purported to be due to 1) The aggressive nature of a specific strain of bacteria to eliminate resident pathogens, 2) The release of antibiotics or other chemicals, which act to mitigate the efforts of pathogens, or 3) The release of vitamins or enzymes that are believed to improve the health of the immune system. The prior art also recognizes the use of cytokines to stimulate certain immune responses. However cytokines are toxic and can induce lethal septic shock. None of the prior art teaches that harmless bacteria release specific ORN to which the immune system has adapted an alert response. The present inventor believes that ORN are the molecules responsible for the healthful benefits derived from consuming probiotics or fermented dairy products. Such benefits can be obtained by administering either bacteria containing ORN or the purified ORN themselves released by bacteria.

U.S. Pat. No. 4,975,467 teaches methods by which synthetic compounds can be used to inhibit the release of IL-1 thereby alleviating the induction of its pathophysiologic conditions. U.S. Pat. No. 5,055,447 provides methods and compositions for the prevention of septic shock by administering growth factor-β. This patent teaches the use of administering a signal compound to intercept or modify existing signals. U.S. Pat. Nos. 5,041,427 and 5,158,939 teach the use of a non-toxic LPS from $R.\ spaeroides$, ATCC 17023 to desensitize macrophages to toxic LPS. Since $R.\ spaeroides$ has an unusual lipid A structure, it may not be effective as a desensitizing agent. U.S. Pat. No. 5,157,039 supports the clinical importance for controlling IL-1 release by macrophages by teaching the use of two non-natural quinolinol compounds, which appear to be non-selective in IL inhibition. U.S. Pat. No. 5,840,318 teaches that bacteria exposed to a neutral pH buffer for 10-16 hours release compounds <10 kDa in size having a UV maximum absorption at 254 nm (A-254). Feeding the <10 kDa sizes activates and modulates an animal's immune system, thereby protecting it against a subsequent lethal challenge of endotoxin. The accumulation of A-254 absorbing compounds in bacteria is associated with the slowing or termination of cell growth. Further, U.S. Pat. No. 6,589,771 B1 teaches that bacteria enter dormancy during their stationary phase by accumulating solutes that increase the cytoplasmic osmolality and H+ which decrease the intracellular pH of the cell. Putting dormant cells in buffers with osmolalities and hydrogen ion (H+) concentrations lower than that of the cell will force the diffusion of solutes and H+ thereby inducing the activation of the cell. Rather than a single 10-16 hour wash to induce the release of the compounds that have a maximum of UV absorption at 254 nm, one can employ a series of 20-minute washings in a buffer of pH 7 and of an osmolality lower than the cell's followed by an adjustment period of approximately 72 hours in the final wash.

Livestock are routinely fed silage, a product containing high levels of viable and harmless *Lactobacillus plantarum*. When ingested and chewed as cud, the silage bacteria release immune-activating ORN. The proper selection of harmless bacteria that ferment silage and grains and also release biologically significant levels of ORNs will help improve the health of livestock.

Direct-fed microbials and probiotics are harmless bacteria which are grown in a rich media, concentrated, dried and fed to animals either as a powder for top-dressing or in gel forms for oral inoculation. On occasion some of these products have been shown to provide a health benefit to the animal in combating infections relating to shipping and weaning. However, analyses of commercial products indicate a low concentration of ORNs as well as their inadequate release when transferred to saliva or to a nutrient-reduced environment. This inventor has determined that the generally accepted methods for preparing probiotics do not allow for the accumulation or retention of significant levels of ORN. It is believed that uncontrolled unit operations during production may occasionally and randomly produce a finished product containing adequate levels of ORN-releasing viable bacteria. These uncontrolled production parameters explain the occasional effectiveness reported for some probiotics. This invention puts forth the production and storage parameters, which yield a bacterial preparation that permits the administration of a stable, probiotic of known bacterial dose or one containing sterile ORN for livestock and poultry. Currently, viability of probiotics is believed necessary for effectiveness. However, this invention allows for the distribution of a sterile, stable product that can be stored without refrigeration and would provide a known dose of a measurable chemical.

The present inventor has found that the extrusion of ORN from the cell is forced by transferring bacteria which have accumulated ORN into environments of a lower molality and lower H+ concentration than that of the bacterial cell, e.g. saliva, body fluids and physiologic saline. Extrusion can be induced by subjecting the bacterial populations to repeated dilutions or washings, as many as 6, in pH neutral buffers of sufficient molarity to maintain a neutral pH in the presence of the efflux of H+ that accompany ORN. Further, the present inventor has discovered doses of ORN that are also effective in rescuing monocytes from apoptosis and, in addition, rescue animals from the lethality of endotoxemia. Moreover, lab tests have been developed which aid in the selection and screening of bacteria, which release the more potent ORN and determining appropriate doses.

ORN are the products of the destruction of ribosomal RNA, which occurs concomitantly with the slowing of bacterial growth. The number of ribosomes is known to be directly proportional to the rate of growth of bacteria. Fast growing populations are known to possess 70,000 ribosomes per bacterial cell while cells in slow-growing population have as few as 2000 ribosomes. (Neidardt, F. C., Ingraham, J. L. and Schaechter, M., in The Physiology of the Bacterial Cell, Sinauer Assoc., Sunderland, Mass., 1990, p 430). As exponential growth slows, ribosomal RNA is hydrolyzed, creating very acidic oligoribonucleotides, which accumulate in the cytoplasm and in the broth. With accumulation of ORNs by the cytoplasm, the lag period extends into days and even weeks.

The hydrolysis of ribosomal RNA requires conditions of neutral pH from about 6 to about 9 but preferably from about 6 to about 8. However, acidic conditions (a pH of or less than 6) are required for the formation and stabilization of the ORN:DNA complex. The first of this two-step reaction is accomplished during the growth of bacteria in neutral broths. At about the mid-exponential growth point (5-8 hrs), H+ begin to be released along with ORNs from the hydrolysis of RNA.

In the manufacture of probiotics the culture broth of bacteria is artificially maintained at neutral pH in order to prevent the slowing of growth and thereby maximizing production of the bacteria for sale. Sodium hydroxide is commonly added to resist the culture's natural tendency towards a lower pH. Short production times and large cell masses are the goals of probiotic manufacturers and are achieved by not allowing the pH of the media to become acidic.

However, under these common practices, ORN may be formed but are not retained in the bacteria. According to the generally-accepted practices, the probiotic bacteria are then concentrated by centrifugation or filtration at neutral pH. Under these pH conditions, the ORN cannot bind the genomic DNA, and are lost to the supernatant, which is flushed down the drain.

The ORN that are most effective in boosting an immune response are those between 0.5 and 10 kDa. They are a new rich source of natural, normally-occurring, co-evolutionarily evolved immune modulators that can be safely used to protect animals and humans from infections and over-stimulation of their immune system. In Pending U.S. patent application Ser. No. 09/883,550 ORNs, ranging from 0.5 to 10. kDa, have been shown to activate and modulate macrophages by adjusting the expression of individual surface receptors on macrophages, thereby re-centering a dysfunctional immune system. Furthermore, human cell culture and in vivo animal testing indicate the potential role of ORN<10 kDa as adjuvants by stimulating the production of antibodies. Results from stimulating human B-cells in cell culture and in mice demonstrate increased B-cell activity when an experimental vaccine against melanoma was injected with ORN<10 kDa. Furthermore, in Pending U.S. patent application Ser. No. 09/883,550 in vitro testing indicates the ORN potential role as adjuvants by stimulating the release of IL-12. See U.S. Pat. No. 5,840,318. Studies with Balb/C mice have revealed that the consumption or injection of sterile preparations of ORNs in this range are non-toxic to the mice and provide the mice protection against a subsequent lethal challenge of injected endotoxins. See U.S. Pat. No. 5,840,318.

Because of the ORN potential as immune modulators, the discovery of the release of immune-activating and modulating factors has broad implications to improving the immune response through diets and pharmaceutical preparations for humans and animals. Numerous patents teach the healthful benefits of administering specific viable bacteria to humans and animals either orally or parenterally to provide local immune stimulation. For example, direct-fed microbials and probiotics, harmless bacteria which are grown in a rich media, concentrated, and dried, may be fed to animals either as a powder for top-dressing or in gel forms for oral inoculation. See U.S. Pat. Nos. 6,797,266; 6,461,607; and 5,401,501. These products are intended to provide a health benefit to the animal in combating infections relating to shipping and weaning.

However, many products marketed as containing probiotics are perceived as over-hyped. J Appl Bacteriol. 1989 May; 66(5):365-78. Clinical testing of probiotic-containing products has generated inconsistent and equivocal results regarding the products' claims. J. Nut. 2000; 130:384S-390S, Nut. Rev. 2003 March; 61(3):91-9. In short, many probiotics claims are unsubstantiated or simply fail to demonstrate any health benefit. The inventor believes that ORN are the molecular mode of action of probiotics and are lost during the presently accepted general methods of producing probiotics. While the prior art recognizes the importance of modulating the immune system, it does not teach the parameters of production to provide a significant level of ORNs which are safe, natural, normally occurring biological chemicals derived from co-evolution, which are effective when taken orally or parenterally.

To date, thirteen different species of animal-associated bacteria have been found to release ORN<10 kDa when stressed. See U.S. Pat. No. 5,840,318. However, the distribution of polymer:oligomer:monomer is not equal amongst these species. See U.S. Pat. No. 5,840,318. Therefore, not all strains of bacteria, even of the same species, release levels of ORN<10 kDa sufficient to protect animals against a subsequent bacterial invasion. Therefore, for these and other reasons, there is a need for the present invention.

It is an object of the present invention to provide a method for the accumulation of ORN in bacteria.

It is an object of the present invention to provide a method for the retention of ORN in bacteria.

It is an object of the present invention to provide a method for preventing the loss of ORN during bacterial production or storage.

It is an object of the present invention to provide an isolated bacterium comprising ORN less than 10,000 Daltons in molecular size.

It is an object of the present invention to provide isolated ORN that are less than 10,000 Daltons in molecular size.

It is an object of the present invention to provide a method of preparing an immune-enhancing animal feed or animal drinking water comprising ORN.

It is an object of the present invention to provide a method of preparing an immune-enhancing animal feed or animal drinking water comprising bacteria having ORN.

It is an object of the present invention to provide a method of enhancing the immune system of an animal or its resistance to infection.

The method and means of accomplishing each of the above objectives as well as others will become apparent from the detailed description of the invention, which follows hereafter.

SUMMARY OF THE INVENTION

The present inventor is the first to recognize that oligoribonucleotides <10 kDa (ORN) are retained in bacteria when growing bacteria are allowed to acidify the growth medium. Surprisingly, the present inventor has identified that ORN are accumulated and retained within the cell if maintained in an environment that has a pH of or less than 6 or concentrated at a pH of or less than 6 to a density of less than 3 billion cells per cubic centimeter. Subsequently, these ORN are released from a bacterial cell upon encountering a neutral pH environment or overcrowding.

In one embodiment, the invention provides a method of producing immune-enhancing, bacterial derived ribonucleotides (ORN) in bacteria comprising growing bacteria in a medium wherein the initial pH of said medium is neutral. In one aspect of the present invention, the genera of bacteria for use in accumulating ORN include but, are not limited to, Lactobacillus, Bifidobacterium, Staphylococcus, Streptococcus, Pseudomonas, Propionibacterium, Bacillus, Escherichia, Enterococcus, and mixtures thereof. The bacteria are allowed to grow naturally, acidifying the medium so that the ORNs, released by the destruction of ribosomal RNA, are accumulated in the bacterial cytoplasm and then the bacteria are concentrated at a pH of or less than 6 and/or to a density of less than 3 billion cells per cubic centimeter or mL. In yet another embodiment, the bacteria concentrated at a pH of 6 or less are washed with water or other liquid having a pH of 6 or less to maintain the retention of ORN within the bacteria. The release of the ORN from bacteria is greatly retarded using wash-waters having a pH of 6 or less. In contrast, use of wash-waters with a pH greater than 6 can force ORN out of the bacterial cell.

The present inventor teaches a method of preventing the loss of ORN from bacteria during storage by storing the bacteria in a suspension maintained at a pH of or less than 6, and preferably in a suspension at a pH from about 2.5 to about 5.5. In one aspect, the suspension is media in which bacteria may be grown or have been grown. In another aspect, the genera of the bacteria for use with the present invention may include but, are not limited to, Lactobacillus, Bifidobacterium, Staphylococcus, Streptococcus, Pseudomonas, Propionibacterium, Bacillus, Escherichia, Enterococcus. In another embodiment, the invention provides a composition comprising isolated ORN that are less than 10,000 daltons in molecular size.

The invention also discloses compositions and methods for preparing an immune-enhancing animal feed or animal drinking water for animal consumption by admixing the ORN or bacteria comprising ORN with animal feed or animal drinking water. In yet another embodiment, the invention provides for a method for enhancing the immune system of an animal and/or its resistance to infection comprising administering to an animal a therapeutically effective amount of ORN<10 kDa or bacteria comprising ORN<10 kDa.

These and other embodiments of the invention will become apparent upon reference to the following Detailed Description. All references disclosed herein are hereby incorporated by reference in their entireties as if each was incorporated individually.

BRIEF DESCRIPTION OF THE DRAWINGS

A known standard of free uracil eluted at 20-25 mL, corresponding to Peak III. Furthermore, thin layer chromatography of Peak III in two different solvents had the same $R_f$ value as free uracil (see Example 11). Peaks II and IV most likely contained penta-, tetra-, tri-, di- and mononucleotides.

FIG. 2 is an instrument tracing of a sample of the ORN<10 kDa released by L. monocytogenes in a single 20 min. washing in 0.1M PBS, pH 7.3 chromatographed on HPLC. The tracing at 220 nm of ORNs separated by HPLC indicates the presence of two groups, one hydrophobic and one hydrophilic. Each group appears to contain about 6 ORN each. Those in the hydrophobic group could be as large as 30-mers while the smaller hydrophilic ones are likely to be the penta-, tetra-, tri-, di- and mononucleotides and free uracil observed separated on Sephadex G-10 shown in FIG. 1.

The column was an RP-318, 250 cm×4.6 mm. A 2-solvent system was used to elute the ORN: 0.1% trifluoroacetate, and 80% methyl cyanide in 0.1% trifluoroacetate. The hydrophilic compounds were eluted 7 min after the flow of 0.1% trifluoroacetate was started. The hydrophobic group was eluted 38 min after the start of the second solvent of 80% methyl cyanide in 0.1% trifluoracetate solvent. The presence of the compounds was detected by absorption at 220 nm.

DESCRIPTION OF THE INVENTION

The methods by which the objects, features and advantages of the present invention are achieved will now be described in more detail. These particulars provide a more precise description of the invention for the purpose of enabling one of ordinary skill in the art to practice the invention, but without limiting the invention to the specific embodiments described. All references cited herein are hereby expressly incorporated by reference.

DEFINITIONS

For purposes of this application the following terms shall have the definitions recited herein. Units, prefixes, and symbols may be denoted in their SI accepted form.

As used herein and in the appended claims, the singular forms "a", "an" and "the" include plural references unless the context clearly dictates otherwise.

As used herein, the term "<10 kDa" refers to substances that are sufficiently small to pass through a molecular filter designed to retain molecules larger than 10,000 Daltons.

As used herein, the term "<10 kDa ORN" refers to oligoribonucleotides resulting from the hydrolyses of the ribonucleic acids found in bacterial ribosomes.

As used herein, the term "accumulate" refers to a bacterium amassing ORN or increasing ORN levels, as opposed to diminishing or lessening ORN levels within the bacterium.

As used herein, the term "acidify" refers to making a solution, buffer, or medium become acidic.

The term "arousing" as used herein includes causing dormant cells to revert to their vegetative states. The vegetative state is marked by its ability to propagate in broths or on agar media developed for their growth and identification during the time period allotted the visible observation of colonies (2-3 days) with the naked eye.

As used herein, the term "buffer" refers to a solution of chemicals chosen to provide a desired pH having a prescribed molar concentration. Two buffers were used: an acetate buffer to provide acid pH values and a phosphate buffer to provide a neutral pH. (See Chapter 16, "Preparation of Buffers" by G. Gomori, p 138; in Methods in Enzymology, Vol II, ed: Colowick, S. P. and Kaplan, N. O., Academic Press, Inc., New York, 1954-1963.) As used herein, the terms "cellular immune system" and "humoral immune system" are known to those of skill in the art.

The term "collecting" as used herein refers to the gathering of bacteria, including bacteria in which ORN have been retained.

The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

The term "dormant" bacteria as used herein includes (a) bacterial cells that are "viable but not culturable" or "quiescent" or "nascent" or "planktonic" which may or may not be metabolically active. Dormant forms of bacteria are those that do not propagate on agar media formulated for their growth and identification during the time period allotted for the observation of colonies (2-3 days) with the naked eye.

The term "effective concentration or amount" for enhancing the immune system as used herein includes a concentration or amount of ORN capable of: (1) modulating an animal's immune system to rescue monocytes from apoptosis, (2) modulating a mammal's immune system to adjust the expression of individual surface receptors on macrophages to re-center a dysfunctional immune system, (3) stimulating a mammal's immune system to its highest potential so that the immune system responds to an infection at its complete power; (4) stimulating a mammal's immune system to provide protection against microbial invasions; (5) prevent the occurrence of auto-immune diseases as well as other diseases symptomatic of an unrestrained immune system; and (6) protect an animal against the lethality of endotoxemia.

By way of example, an effective concentration or amount of ORN admixed with animal feed or drinking water will stimulate the immune system. Generally, the ORN will be isolated or contained in a composition such as an immune-enhancing animal feed or drinking water to provide ORN at a concentration of about 1-300 µg per kg of body weight. A concentration of 300 µg per kg of body weight will provide the highest level of protection as listed above: (6) protect an animal against the lethality of endotoxemia. To achieve (1) the lowest level to modulate an animal's immune system to rescue monocytes from apoptosis is approximately one-twentieth or 15 µg per kg of body weight. Of course, variation between species of animal, as is well known in general drug responses, will be found within and beyond this range of 15-300 µg per kg of the animal's body weight.

The terms "enhancing the immune system" or "immune-enhancing" as used herein includes (1) stimulating a mammal's immune system to provide protection against microbial invasions, the lethality of endotoxemia, and the occurrence of auto-immune diseases as well as other diseases symptomatic of an unrestrained immune system; (2) stimulating a mammal's immune system to its highest potential so that the immune system responds to an infection at its complete power; (3) modulating a mammal's immune system to adjust the expression of individual surface receptors on macrophages to re-center a dysfunctional immune system; and (4) modulating a mammal's immune system to rescue monocytes from apoptosis.

As used herein, the term "growth medium", "medium" or "media" refers to a medium that is capable of supporting the growth of cell populations in vitro.

The term "hypermutative" defines bacterial cells that display an increased rate of mutation and form mutants that are very different from mutants occurring from mutations seen at normal mutation rates. For example, hypermutants exhibit polymorphism on agar plates and display significant changes in their metabolic enzymes and antibiotic susceptibilities such that they may no longer be typed as the same species. As used herein, the term "hypermutative" depicts changes in the characteristics of bacteria that have been subjected to 2-6 serial stresses of washing in pH neutral buffers.

As used herein, the term "immune-enhancing, bacterial-derived ribonucleotides" refers to oligoribonucleotides (ORN) produced by the destruction of ribosomal RNA, which occurs concomitantly with the slowing of bacterial growth. When encountering normal and naturally-occurring stresses such as those described herein and in U.S. Pat. Nos. 5,840,318 and 6,589,771, bacteria release stress release factors including a mixture of immune-enhancing, bacterial-derived ribonucleotides. The immune-enhancing, bacterial-derived ribonucleotides of the invention typically ranging from 1-30 nucleotides in length and have a molecular weight <10 kDa, in particular, between 500 and 3,000 Da. They are readily absorbed, are non-toxic when fed or injected into mice, demonstrated to protect mice against a subsequent lethal challenge of injected endotoxin and modulate and/or activate macrophages. See pending U.S. patent application Ser. No. 09/883,550.

An unusual feature of the "immune-enhancing, bacterial-derived ribonucleotides" is their resistance to hydrolysis by RNase (product R-7003 purchased from Sigma Chemical Co.) when used as directed by the manufacturer (incubating 750 µL of "immune-enhancing, bacterial-derived ribonucleotides" with 50 µg of RNase at 37° C. for 3 hr). The resistance of these ORN<10 kDa to RNase suggests that the ORN have unusual structures. Additionally, it is hypothesized that at least some of these ORN may have substitutions on their bases and ribose (e.g., methyl and other groups) or may have nucleotide strands held together by complementary hydrogen bonding with itself. These unusual structural conditions leading to resistance to RNase are believed to be responsible for the ORN's unique stimulation and modulation of the immune system. It should be noted that throughout the application, the terms ORN and immune-enhancing, bacterial-derived ORN are used interchangeably.

Bacterial genome replication is mediated by DnaA, a protein that reacts with specific sequences in what have been named "initiation boxes" which occur within a specific region of the genome named "the Origin of Replication" oriC. Four to 12 initiation boxes usually occur within the oriC of various species and genera of bacteria. The reaction of DnaA with one or more of the initiation boxes triggers replication of the entire genome. Any interference of DnaA binding to the boxes will slow or prevent replication.

Initiation boxes contain a stretch of about 9 deoxynucleotides with conserved regions of A and T. For example, *E. coli* has four initiation boxes 5'TGTGG<u>ATAA</u>3' (opposing strand: 3'ACACC<u>TATT</u>5'), 5'GG<u>TTATA</u>CAC3' SEQ ID NO: 1) (3'CC<u>AATAT</u>GTG5'; SEQ ID NO: 2), 5'<u>TTT</u>GG<u>ATAA</u>3', (3' AAACC<u>TATT</u>5') and 5'<u>TTAT</u>CCACA3' (3' AATAGGTGT5'). It can be seen that sequences containing T and A are well conserved. This is true across many bacterial genera.

It is believed therefore that sequences of ribosomal ORN rich in A and U are responsible for the lag period in bacterial growth. As these ORN are released by the destruction and hydrolyses of ribosomes, they form hydrogen bonds with the complementary ODN in the initiation boxes thereby slowing DNA replication and cell reproduction.

Because of their unique structure and role in bacterial growth the immune system has learned to be sensitive to their sudden appearance. Their release when encountering physiologic conditions signals the immune system that bacteria are ramping up their rates of growth; dormant forms are reverting to their vegetative states.

It is therefore believed that ORN rich in adenine-uracil or uracil-adenine sequences may be particularly effective in enhancing the immune system. Without wishing to be bound by this theory, it is believed that ORN rich in AU and UA sequences and less than 10 nucleotides in length form complementary complexes with the bacterial cytoplasmic deoxyribonucleic acid (DNA), including the Origin of Replication (oriC) initiation boxes, under an acidic pH. Such complexing prevents the binding of the initiation protein DnaA necessary for the start of DNA replication, resulting in a decreased rate of bacterial replication. Examples of ORN rich in AU and UA sequences suitable as binders to DnaA and as blockers of the initiation boxes include tri-, tetra- and penta-ribonucleotide sequences capable of forming strong complementary bonds to the tri-, tetra- and penta-deoxynucleotide sequences (underscored above) in the initiation boxes are UAUU, AAUAU, AAA, UAUU and AAUA and for the opposing strands: AUAA, UUAUA, UUU, AUAA and UUAU. Free uracil and adenine, along with the parts thereof, AAA, UUU, AAUA, UUAU, AUAA, UAUU, AAUAU, and UUAUA are also contemplated to be effective.

As used herein, the term "immune system" refers to the cellular immune system as well as the subject's humoral immune system.

As used herein, the term "incubating" refers to keeping the bacteria in bacterial culture conditions, for example, medium, temperature, aeration, humidity, that would facilitate bacterial growth.

As used herein, the term "microbe" refers to any organism too small to be visible to the naked eye and includes bacteria, fungi, protozoa and viruses.

As used herein, "modulating a mammal's immune response" means increasing or decreasing either the amount of a component of the immune system or the activity by which a component of the immune system is characterized, increasing or decreasing the amount of receptor present on the surface of an immune cell, or increasing or decreasing the number of immune cells present in the mammal.

As used herein, the term "neutral pH" is meant to cover a pH range from about 6.0 to about 9.0, preferably from about 6.0 to about 8.0.

As used herein, the term "preventing" refers to reducing, minimizing, or completely eliminating such loss or damage of ORNs. As used herein, "preventing" may include, for example, at least about a 15% reduction of loss or damage, more preferably at least about 25%, more preferably at least about 50%, even more preferably at least about 75%, even more preferably at least about 80%, even more preferably at least about 85%, even more preferably at least about 90%, even more preferably at least about 95%, and most preferably about 100%.

As used herein, the term "retention" refers to a bacterium keeping possession of ORNs as opposed to extruding or releasing ORNs.

As used herein, "stimulating an animal's immune response" means increasing the amount of a component of the immune system or the activity by which a component of the immune system is characterized, increasing the amount of receptor present on the surface of an immune cell, or increasing the number of immune cells present in the mammal.

As used herein, the term "suspension" refers to a homogeneous mixture of particles that do not readily settle out or precipitate, for example, bacteria in a solution such as bacterial growth medium or buffer.

As used herein, "therapeutically effective amount" refers to an amount, which is effective in reducing, eliminating, treating, preventing or controlling the symptoms of the herein-described diseases, disorders, or conditions, for example, a therapeutically effective amount of ORNs will provide protection against endotoxemia.

As used herein, unless otherwise defined in conjunction with specific diseases or disorders, the term "treating" refers to: (i) preventing a disease, disorder or condition from occurring in an animal or human that may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

As used herein, the term "vegetative" form of dormant bacteria, as used herein, is that form of the bacterial cell from which the dormant cell was formed and reverts to, after arousal and can grow on appropriate media within the limits of times imposed by accepted standard methods (2-3 days).

As used herein, the term "wash-water" refers to pure water or aqueous compositions that may additionally contain sodium chloride and/or buffers of stated molalities and pH, for example, an "isotonic saline" wash-water having 0.9% saline by weight. Washing bacterial cells serves to remove any traces of the media or metabolic products adhering to the surface of the bacterial cells.

It has been known since 1958 that the number of ribosomes per bacterial cell reflects the growth rate of the cell. (Physiology of the Bacterial Cell, Neidhardt, F. C., Ingraham, J. L., and Schaechter, M., Sinauer Assoc., Sunderland, Mass., 1990, p. 422). This is a logical relationship since ribosomes are the "factories" of the cell, translating messenger RNA (mRNA) into proteins. Ribosomes consist of 57 proteins and 3 rRNA molecules (5S, 16S and 23S). As the cell population reaches its maximum density, the ribosomes disappear as they begin to destruct half way through the exponential growth phase. (Davis, B. R., S. M. Luger, and P. C. Tai. 1986. Role of ribosome degradation in the death of starved *E. coli* cells. J. Bact. 166:439-45).

It is currently believed that the disappearance or loss of ribosomes forces the slowing of cell growth. The present inventor has discovered that the slowing of cell replication is accompanied not only by the loss of ribosomes but also by the accumulation of fragments of rRNA by genomic DNA. The present inventor is first to discover that ribosomal RNA (rRNA) is the source of the oligoribonucleotides (ORN). ORN start to accumulate in the cytoplasm of the cell as rRNA is hydrolyzed. As bacteria mature through their stationary phase, ORN continue to associate with the genomic DNA extending the lag period into deep dormancy, marked by the cell's resistance to antibiotics and pasteurization. Only 1 cell in every 500-1000 successfully enters and exits dormancy with the vast majority of cells accumulating ORN improperly, leading to irreversible denaturation and death.

However, cells transferred into pH neutral environments lose ORN from their cytoplasm and can thereby restart cell growth and lose their lagging condition. One way of accomplishing the release of ORN from the cytoplasm is to expose bacterial cells containing ORN to neutral aqueous environments, e.g., saliva, body fluids and physiologic saline. This induces the release of ORN from the cell. For example, release can be induced by subjecting the bacterial populations to repeated dilutions or washings, as many as 6, in pH neutral buffers of sufficient molarity to offset the efflux of H+ that accompany the ORN. Release begins immediately when the cells encounter a pH neutral environment. The present inventor is first to discover that bacteria accumulate ORN or release them when entering pH neutral environments like those naturally occurring in animal fluids.

Through cohabitation, the immune system has adapted an alert response to the presence of ORN, learning that their appearance reflects the restarting of exponential growth by the bacteria and the likelihood of an ensuing infection. The inventor discovered that feeding or injecting ORN smaller than 10 kDa protects mice against the lethality of a subsequent challenge of endotoxin. ORN released by harmless as well as pathogenic bacteria are effective and appear to be nontoxic. Protection of all the mice is afforded only if the ORN are administered 32-96 hours before the lethal injection of endotoxin.

The present invention teaches that this phenomenon is the molecular mode of action of the health benefits observed from feeding harmless bacteria in the form of probiotics or fermented dairy products. Numerous clinical trials have been conducted to support the theory first proposed by Elie Metchnikoff in 1917 with mixed results. Trials in which yogurts were consumed have led to more successful results against viral, bacterial and protozoan infections than those in which purified bacteria were fed. The inventor asserts that the explanation for the differing results is that probiotic bacteria were grown under conditions in which their media was buffered to stay at neutral and washed during processing and before consumption by individuals in the trial, thereby losing the benefits of the accumulated ORN, whereas yogurts were not washed. (For examples see: Yolken R. H., Saavedra J. M., Bauman N. A., Oung I., Perman J. A., 1994 Feeding of *B. bifidum* and *S. thermophilus* to infants in hospital for prevention of diarrhea and shedding of rotavirus. Lancet 344:1046-9 and Hilton, E., Isenberg, H. D., Alperstein, P., France, K., Borenstein, M. T., 1992. Ingestion of Yogurt Containing *L. acidophilus* as Prophylaxis for Candidal Vaginitis. Ann. Inter. Med. 116: 353-7 and Meydani S. N., Ha W-K. Immunologic effects of yogurt. Am J Clin Nutr 2000, 71:861-72).

Before permitting health claims the Food and Drug Administration requires a research-based explanation of the molecular and cellular mode of action of the product. The current invention suggests that the learned response adapted through co-evolution to the release of ORN meets the Agency's requirement.

The ORN of the invention may be administered orally, parenterally, topically, or intranasally to stimulate the immune system by: (1) activating macrophages to release cytokines, in particular IL-1, IL-6 and TNF required to initiate an immune response to prevent or reduce infection, (2) by counteracting the potential pathologic role of macrophages in over-stimulating the inflammatory response locally (for example rheumatoid arthritis and other auto-immune diseases) or systemically (for example septic shock), and (3) by rescuing monocytes from apoptosis.

Circulating monocytes lose viability after 24 hours via apoptosis when cultured in the absence of a stimulus. The administration of ORN has been found to extend the life of the monocyte population from 24 hours to 72 hours, thereby allowing them to mature into macrophages and extend their ability to fight virulent infections.

The methods of obtaining ORN of the invention comprise growing selected bacteria in a media outside of the animal to a selected level of enumeration, and collecting the bacteria under acidic conditions such that accumulated ORN are retained. The collected bacteria are serially washed in pH neutral buffers to force their extrusion of ORNs and the serial wash-waters combined. Bacteria are removed from the serial wash-waters by passing the combined extracts through a 0.22 µm filter. ORN smaller than 10 kDa are collected by passing the bacteria-free combined extracts through a molecular filter with a cut-off at 10 kDa.

The life cycle of bacteria encompasses a pre-growth phase (lag), a growth phase in which division greatly exceed death (log), a phase in which growth rates approximate death rates (stationary), and a decline phase in which death greatly exceeds growth (death phase). Strains in their death phases are not reliable sources of strong ORN. It has now been found that the method of stressing the bacteria is most preferably performed by removing the bacteria from their media while in their late growth phase or stationary phase (about $10^{8-9}$ viable colony-forming units (CFUs) per mL) and re-suspending them at the same cell density in a non-nutritive phosphate buffer at pH 7.6 for sequential stresses of periods of 10-20 minutes at 37°-41° C. The non-nutritive phosphate buffer is preferably phosphate buffered saline (PBS) which is representative of animal secretions, e.g. saliva. More ORN are produced by growing feral strains rather than lab strains to their stationary phase on agar or in broth at their optimum temperatures for growth.

Sequential stressing can be performed in a number of ways. A convenient means of sequential stressing is to transfer the bacteria from their growth medium into fresh PBS. This transfer is marked by the immediate release of ORN. Centrifuging down the bacteria, removing and saving the extract, and adding fresh PBS induces the release of additional ORN. This can be repeated 6 times in order to force the extrusion of all the accumulated ORN. A preferred method is to employ endotoxin-free, 0.1M phosphate-buffer-saline at pH 7.6 in serial washings which mimic physiologic conditions: the dynamic action of bathing and transporting foreign bacteria in body fluids. In some instances to facilitate the release of ORN from bacterial cells, it may be desirable to maintain a neutral pH of the solution, for example, wash-water, medium, suspension, or buffer, to which the bacteria are exposed as H+ ions stream out of the bacteria. One way in which a neutral pH can be maintained is using a buffer having a molality that is greater or equal to 0.1. The present inventor believes that buffers having a molality less than 0.1 M will be insufficient in offsetting H+ ions released by the bacteria so that a neutral pH of the medium or suspension is not able to be maintained. The appearance of ORN can be followed by monitoring absorbencies in the ultraviolet, at 220 nm and preferably at 254 nm.

It was discovered that supernatants containing ORN with a molecular size greater than 10 kDa were toxic when administered parenterally to mice, so in a preferred embodiment, the invention comprises removing all substances greater than 10 kDa by means such as filtration. Thus, the supernatant is filtered so that all ORN greater than 10 kDa are removed and those of a size less than 10 kDa are retained in the PBS solution.

The amount of total ORN released depends on: (a) the age of the bacteria in the growth media; younger cells, for example, those cells formed when the population density of a growing bacterial population reaches 10% of the final density, i.e. $10^{7-8}$ CFU/mL of a bacterial population that eventually reaches $10^9$ CFU per mL, contain levels of more effective ORN; (b) strains selected from the wild provide more ORN than laboratory strains because they grow faster, have more ribosomes and therefore more ORN potentially effective; however, stressing laboratory strains and re-propagating them results in growth rates and the accumulation of ORN similar to feral strains, (c) the pH of the wash-water; pH values at 4.8 induce the release of approximately one-fourth the level of ORN released at pH 7.6; (e) the time; while release begins immediately, it has now been discovered that short sequential periods of stress of 5 to 20 minutes produce more potent ORN than a single stress of time equal to the sum of the multiple stresses. Serial stresses, for example, subjecting the bacterial population to fresh buffer (of a neutral pH), may prevent the acidification of the buffer by H+ ions streaming out of the bacteria.

Generally, for collection of ORN of the invention, the ORN-containing supernatant is rendered bacteria-free by filtering through a 0.22 μm filter to yield a sterile preparation containing all sizes of ORN. Typically, the total ORN fraction consists of 5-20% polymers larger than 30 kDa, and 80-95% oligomers <30. The oligomeric fraction between <10 kDa is non-toxic, readily absorbable, activates macrophages, and extends the viability of monocytes. Daily injections of a protective dose of <10 kDa ORN for five consecutive days did not cause apparent toxicity in mice, i.e. cessation of eating, ruffled fur, huddling, or diarrhea.

Since the ultraviolet spectrum of the composite of ORN indicates a maximum of 254 nm, the absorbancy at 254 nm can be used to monitor their release. One Arbitrary Unit (AU) of ORN was established as that level providing an optical density of 0.001 through 1 centimeter (cm) of a solution. A reading of 1.0 at 254 nm corresponds to approximately 35 μg of ORN. See Molecular Cloning, T. Maniatis, E. F. Fritsch, and J. Sambrook. (1982), in particular pages 61-62, 68, 442 and 444.

ORN from 15 strains of animal-associated, Gram-positive and Gram-negative, aerobic and anaerobic bacteria representing both harmless and virulent pathogens release ORN as evidenced by the rise in A-254 during stress induced by nutrient reduction at neutral pH. However, the distribution of sizes within <10 kDa was not equal across all strains.

This invention teaches the selection of organisms and the conditions employed to grow them to accumulate and retain a maximum level of immunopotent ORN<10 kDa. This invention teaches the improvement of two natural conditions: the consumption of food by humans or feedstuffs by livestock, which are rich in microbial populations. Pasteurized fresh milk contains less than $10^4$ CFU of bacteria per mL, whereas unpasteurized contains 10,000 times more bacteria per mL. Fermented dairy products (such as milk, yogurts, and cheeses) typically contain $10^8$ CFU per mL of populations of harmless bacteria in stationery phase. When transferred by eating into a nutrient poor environment of neutral pH, the mouth, ORN are released at corresponding levels. It is this action, which the present invention explains the frequently reported observations regarding immune stimulation and the benefits derived from consuming fermented foods. Further, if the dwell-time in the mouth can be increased by adding gelling or thickening agents to the foods, the release of ORN and delivery to oropharyngeal macrophages can be increased.

In addition, fresh vegetables containing high levels of harmless bacteria (e.g. *Lactobacillus plantarum*) will also stimulate local macrophages and extend the viability of monocytes by releasing ORN during eating.

Similarly, the practice of administering oral preparations of $10^{8-10}$ CFU of harmless viable bacteria to livestock to reduce the incidence of infections during shipping and weaning results in the release of ORN by bacteria lyophilized from rich media. Superior products can be formulated by selecting bacteria and employing steps in commercial production, which allows the bacteria to accumulate maximum levels of ORN<10 kDa. Likewise, the use of gels with a pH >6 for the feeding of livestock would induce the release of ORN from the bacteria during product storage and shipment so that at the time of oral introduction into livestock, the maximum level of ORN would be immediately available.

In addition, these bacterial preparations can contain added sterile ORNs to increase their immune stimulating effectiveness. Furthermore, probiotic preparations can be delivered bacteria-free by separating and packaging the active fraction ORN<10 kDa.

Additionally, bacterial innoculants of $10^{8-10}$ CFU per gram of bacteria (*L. plantarum* and *Propionii*) are commonly added to stored grains and crops to assist and speed the fermentation of plant materials into readily available nutrients for livestock. Presently, strains are selected for their ability to propagate rapidly on the targeted grains and crops. The "probiotic"

effect of enhancing the animal's resistance to infection which is often observed from consuming inoculated grains and silages is due to the stimulation of macrophages by ORN<10 kDa released when these bacteria are introduced into the nutrient-poor, pH neutral environment of the animal's mouth. The probiotic effectiveness of crop innoculants can be increased by selecting strains adapted to living on the intended crops plus having the capability to release significant levels of readily-absorbable, non-toxic ORN as taught herein.

The present invention provides isolated ORN and isolated bacteria comprising ORN and methods for preparing an immune-enhancing animal feed or animal drinking water and enhancing an animal's immune response and/or resistance to infection utilizing isolated ORN or bacteria comprising accumulated ORN. The bacteria used in the present invention as provided above may belong to any of a number of genera appropriate for the cattle raiser.

In mouse trials, one embodiment of the present invention comprises an isolated bacterium comprising accumulated ORN. When a preparation of $10^9$ CFU per mL of bacteria is exposed to 0.1M buffer at pH 7.3 for 20 min the bacteria release ORN having an A-254 equal to about 1. In our feeding experiment, female mice weighing 25 g each were saved from the lethality of endotoxemia when fed 0.2 ml of a preparation of bacteria-free ORN<10 kDa having an $A_{254}$ of about 1 corresponding to about 35 µg. 0.2 mL of a 35 µg dose of ORN may be administered as described in Examples 2, 3, and 6, for example, so that a total of 7 µg is delivered to the subject mouse. A dose of 7 µg of ORN translates to one of 280 µg per kg of mouse body weight. A dose corresponding to 28 µg per kg saved one-third of the mice in a separate group. A dose corresponding to 2.8 µg per kg did not save any mice but did activate human monocytes in cell culture as described earlier. Therefore, a dose between 2.8 and 280 µg per kg of mouse body weight modulated the immune system to varying levels that assisted in the defense of the host.

Feeding studies with mice gave a therapeutically effective consensus range of 2.8 to 280 µg per kg. At the low end of the range, animals can be expected to derive a significant clinical benefit by stabilizing their immune response. Feeding the high end of the range will provide a health benefit against serious immune challenges. Anecdotal data was obtained to demonstrate the effectiveness of this range to avian, bovine, porcine, equine, murine, ovine, caprine, canine, and feline species.

The isolated ORN or isolated bacteria comprising ORN provided by the present invention can be added to any animal feed or supplement for livestock or companion animals including, but not limited to, grains or pelleted concentrates, including those commercially available. In addition, the isolated ORN or isolated bacteria comprising ORN provided by the present invention may be incorporated directly into drinking-water, animal feeds or feed supplements, including those feeds that are commercially available. When incorporated directly into animal feeds or drinking water, the present invention may be added to such feeds or waters in amounts calculated to deliver the effective concentration of 2.8-280 mg of ORN<10 kDa per kg of animal weight. In addition, a dosage of bacteria from about 1 to 80 ml of $10^8$ CFU/mL or 0.1 mL to 8 mL of $10^9$ CFU/per kg of animal weight may also be used as effective concentrations when added to animal feeds, drinking water or supplements provided that the bacteria are grown and/or stored under conditions as those described herein or similar conditions so that the bacteria contain about 35 µg of ORN<10 kDa. The AU may be determined by reading the absorbance of a bacteria-free extract at 254 nm. The absorbance at a wavelength of 254 nanometers ($A_{254}$) equals 1000 AU of ORN/mL or cc corresponding to about 35 µg/mL. Alternately, the amount of ORN can be calculated based on the relationship between optical density (OD), absorbance (A) and arbitrary units (AU) so that the amount of ORN can be determined as µg/mL. An OD unit corresponds to the amount of nucleic acid in 35 µg in a 1 mL volume using a 1 cm path length quartz cuvette that results in an $OD_{254}$ reading of 1. A solution containing 35 µg per mL of ORN has an absorbancy (optical density) of 1.0 at a wave length of 254 nm.

This concentration can be given as isolated ORN<10 kDa or as bacteria containing ORN equivalent to 2.8 to 280 µg of ORNs<10 kDa. The amount of bacteria containing 2.8 to 280 µg of ORN<10 kDa will vary depending on a number of growth factors and conditions. Roughly, the amount of ORN per bacteria can be calculated as shown in Example 6. Bacteria grown under the condition described herein to a density of 1 billion bacterial cells per mL will contain about 35 µg of ORN<10 kDa. Therefore, feeding 1 mL of 1 billion bacterial cells per kg to an animal will provide an immune benefit to that animal. The isolated ORN or isolated bacteria comprising ORN contained in the present invention may be fed to any animal, including but not limited to, avian, bovine, porcine, equine, ovine, caprine, canine, feline and human species. One skilled in the art can appreciate that the amount of the isolated ORN or isolated bacteria comprising ORN fed can vary, in addition to the level of effective ORN present as discussed above, depending upon the animal species, size of the animal and the type, volume and pH of feedstuff or drinking water to which the isolated ORN or isolated bacteria comprising ORN is to be added.

In addition, pharmaceutically acceptable carriers may be added to the isolated ORN or isolated bacteria comprising ORN. Pharmaceutically acceptable carriers are generally added that are compatible with the active ingredients (ORN) and acceptable for pharmaceutical use. For example, if the ORN are delivered within bacteria, the carrier should not interfere with their release, e.g. should not be below pH 6. In addition, if the ORN are delivered naked, the carrier should not bind the ORN thereby interfering with their activity. Combinations of carriers may also be used. One of ordinary skill in the art would be familiar with pharmaceutically acceptable carriers and it is described, by way of example, in Remington's Pharmaceutical Sciences, 18th Edition, Mack Publishing Company, Pennsylvania, USA. For example, pharmaceutical carriers include, without limitation, an aerosol spray, powder, stick, granules, cream, paste, dispersion, gel, lotion, emulsion, syrup, ointment, sponge, cotton applicator, topical dressing, dermal patch, cleansing tissue, solution, or suspension. Except insofar as any conventional media or agent is incompatible with the active ingredient, use thereof in the pharmaceutical compositions of the present invention is contemplated. Pharmaceutical compositions for use according to the invention may take a form suitable for oral, buccal, parenteral, nasal, topical or rectal administration, or a form suitable for administration by inhalation or insufflation. The methods for determining dosages, dosage forms, methods of administration and background information concerning ORN would be routine to one skilled in the relevant art.

ORN are not to be confused with shock proteins which are expressed by bacteria in response to changes in temperature or other conditions. Shock proteins have a molecular weight greater than 10 kDa (typically 30-150 kDa) and do not absorb UV with a maximum at 254 nm. They represent increased synthesis of certain proteins plus the de novo synthesis of new proteins.

In an earlier U.S. Pat. No. 5,840,318, before the present invention in which the inventor determined the chemical nature of the accumulated molecules, the ORN were referred to as "stress response factors, SRFs". In U.S. Pat. No. 6,589,771 B1, the invention teaches that ORNs are responsible for the lag period of bacteria and further accumulation with time allows bacteria to extend their lag phase into a state of dormancy in which it is resistant to pasteurization. The forced release of ORN by repeated washings in pH neutral buffers mimics the natural phenomenon of a dormant cell entering a growth-supporting environment and restarting exponential growth. Repeated washings (e.g., 6) induce dormant bacteria, as well as vegetative forms, into a state of hypermutation marked by a dramatic change in colony morphology, metabolic enzymes and sensitivity to antibiotics.

Every vegetative cell of species belonging to the spore-forming genera including but not limited to Bacillus, Clostridium, and Sporosarcina, forms a spore. In contrast, the present invention has found that only approximately 0.1% of the populations of bacteria classified as non-spore formers successfully enter and exit the dormant state. If non spore-forming bacteria properly complex ORN with their genomic DNA, dormancy is reversible but, if executed improperly, which appears to happen in 99.9% of the populations, the complex is irreversible and the cell is dead; it cannot restart replication. However, 0.1% of a bacterial population is sufficient to ensure immortality of that species.

Thus, the present invention teaches that non spore-forming vegetative and dormant bacteria release ORN upon exposure to pH neutral buffers, including saliva and other physiologic fluids. Through cohabitation and co-evolution, the immune system has adapted an alert response to the sudden appearance of ORN. Feeding ORN to mice 36 hours prior to a lethal injection of endotoxin protected them from death. The ORN released during the first and/or second washes, appear to have the greatest efficacy in the mouse and in the macrophage assays. See Example 6. The inventor observed no side effects from feeding or repeated injections of sterile ORN; both harmless and harmful bacteria release protective ORN. Extensive washings trigger the cell to become hypermutative.

The present invention thus teaches the previously unknown effect that serial washes in acidic buffers do not induce the release of ORN and do not trigger the reversion of dormant bacteria to their vegetative reproducing forms. Furthermore, unintentional acidification of a neutral buffer can be forced by the release of relatively high levels of ORN. The osmolality within the cell can be so high as to acidify buffers with a molality of 0.05M. It is surprising to observe that the addition of $10^9$ CFUs of bacteria, which occupy only 1% of the volume or 0.01 mL, to 1 mL of a solution with a pH of 7.3 buffered by phosphate at 0.05M, becomes acidic. Thus, the present inventor believes the molality of the bacterial cytoplasm must be about 5M.

Therefore, the above results of the present invention teach how the feeding or injecting of sterile preparations of ORN can help prevent infections and the onset of toxic shock. Further, elucidation of the mechanisms of their release from the bacteria used to prepare yogurts also provides new insight into the explanation for the health benefits derived from eating fermented foods.

In addition to teaching the release of ORN, the present invention teaches the previously unknown methods of inducing the accumulation and retention of ORN within a cell. It is accepted that bacteria reproduce by means of binary fission: each cell divides to form two new cells. Under nutrient-rich conditions, starting with one cell, growth stops after about 30 generations of cell division when the population reaches about 3 billion cells per cc. When growing in natural habitats or unregulated conditions in the lab, the pH of the media decreases from neutral to about 5 as growth proceeds. The destruction of ribosomes creates acidic ORN, which accumulate in the genome of the cell and in the media, lowering the pH.

The present inventor has discovered that acidic ORN accumulate in the cytoplasm of the bacteria and drive the cytoplasmic pH as low as 2, the $pK_a$ of the phosphate group on the ORN.

The present inventor also contemplates that any species of bacteria may be used in the present invention provided that the bacteria accumulate ribosomal RNA, the destruction of which creates the ORN. The range of 2.8 to 280 μg of ORN per kg is the "effective concentration" to provide an animal with resistance to microbial infection or the lethality of endotoxic shock.

The present inventors contemplate that bacteria may be propagated rapidly, for example, growing bacteria to a density of greater than 100 million bacteria per mL within 24 hours, resulting in the increased synthesis of the number of ribosomes present in the cell, for example, about 80,000 ribosomes per cell. The increased number of ribosomes results in increased amounts of RNA becoming available for hydrolysis, accumulation and eventual release as ORNs. This approach may be advantageous when using slow growing bacteria (like Mycobacterium tuberculosis, L. fermentum, L. acidophilus) that have low levels of ribosomes to produce ORN for accumulation or for extrusion. ORN from harmless bacteria stimulate the alert response as well as those released by pathogenic bacteria. See Examples 2, 3 and 4.

Besides striving to conditions that facilitate a rapid growth rate, there are no particular limitations to the different conditions in the culturing of the bacteria, and the methods that are ordinarily used may be carried out, where bacteria are cultured in suitable media, respectively. General growth conditions for culturing the particular bacteria may be obtained from depositories and from texts known in the art such as Bergey's Manual of Systematic Bacteriology, Vol. 1, Williams and Wilkins, Baltimore/London (1984), N. R. Krieg, ed.

Either complex or chemical media can be used to grow the bacteria. The nutrient medium for the growth of any bacteria should contain sources of assimilable carbon and nitrogen, as well as mineral salts. Suitable sources of assimilable carbon and nitrogen include, but are not limited to, complex mixtures, such as those constituted by biological products of diverse origin, for example soy bean flour, cotton seed flour, lentil flour, pea flour, soluble and insoluble vegetable proteins, corn steep liquor, yeast extract, yeast and casein hydrolysates, peptones and meat extracts. Any sources may be used for the nitrogen source of the medium as long as the bacteria can utilize them. Additional sources of nitrogen include simple, synthesizable organic and inorganic compounds such as ammonium salts, alkali nitrates, amino acids, nitrates, such as ammonium chloride, ammonium sulphate, sodium nitrate and potassium nitrate. Any sources may be used for the carbon source of the medium as long as the bacteria can utilize them. Specifically, there may be used sugars such as glucose, fructose, sucrose, maltose, mannose, glycerin, millet jelly, molasses, dextrin, starch, and sorbitol; alcohols such as methanol, ethanol, and glycerol; organic acids such as fumaric acid, citric acid, acetic acid, and propionic acid and their salts; hydrocarbons such as paraffin; and mixtures of the foregoing. Nutrition sources may also be added appropriately to the medium, which are used in culturing, including inorganic salts, the salts of minute metals, and vitamins. Generally, the nutrient medium may include, but is not limited to, the following ions: $Mg^{++}$, $Na^+$, $K^+$, $Ca^{++}$, $NH_4^+$, $Cl^-$, $SO_4^{--}$, $PO_4^{---}$ and $NO_3^-$ and also ions of the trace elements such as Cu, Fe, Mn, Mo, Zn, Co and Ni. The preferred source of these ions is mineral salts. One skilled in the art would also recognize that various growth media can be employed, for example, Luria Broth (LB), NZCYM Broth, Brain-Heart-Infusion (BHI), Minimal-Media-Davis (MMD), Mann-Rogosa-Sharpe broth (MRS) or simple chemical media. There may also be added to the medium, a substance for inducing the growth of a bacterium. Buffers to maintain neutral or basic pH should be avoided; they will induce the release of ORNs and thereby prevent their accumulation.

One method for the preparation of the selected bacterium comprises inoculating the bacterium from a frozen stock culture prepared as is known in the art (about a 17% glycerol stock) into a flask or a glass tube with a metal closure or a fermentor containing a growth medium (containing an aliquot from a sterile solution which includes Tween 80, glycerol and distilled water) whose composition is described in more detail below. The growth is carried out at temperatures ranging from about 20° C. to about 40° C. One skilled in the art would also recognize that various growth media can be employed, for example, Luria Broth (LB), NZCYM Broth, Brain-Heart-Infusion (BHI), Minimal-Media-Davis (MMD), Mann-Rogosa-Sharpe broth (MRS) or simple chemical media. The pH needs to fall to about 6 or below for the ORN to accumulate inside the cell; at neutral pH, they will be released into the media.

It should be noted that reference to particular buffers, media, suspensions, reagents, contacting or culture conditions, amount of substrate, amount of inducer where used, and the like, in any part of the present disclosure is not intended to be limiting, but should be read to include all such related materials that those of ordinary skill in the art would recognize as being of interest or value in the particular context in which the discussion herein is presented. For example, it is often possible to substitute one buffer or culture medium for another, such that a different but known way is used to achieve the same goals as those to which the use of a suggested method, material or composition is directed.

According to the present invention, one may use naturally occurring or genetically engineered, recombinant, bacteria or mutant bacteria or those resistant to antibiotics to accumulate and/or extrude ORN. Thus, any suitable bacterium, or suitable recombinant or mutant thereof, may be used in the processes of the present invention. As would be understood by those skilled in the art in light of the present disclosure, the conditions of the subject processes would be chosen depending upon, e.g., the kind of bacterium and the particular preparation thereof. For example, the pH, temperature, component concentrations, and the like, e.g., medium, will be chosen to provide the particular desired result using the selected bacterium.

The bacteria suitable for use in the present invention may be prepared by any suitable method known to those skilled in the relevant art. Based upon the present disclosure including the methods provided below, those skilled in the art would understand how to modify any part of these methods, e.g., method of preparing the bacterium, growth medium components and conditions, e.g., temperature, pH and the like; respective incubation conditions; to achieve the desired result using any suitable bacterium.

One skilled in the art can isolate required bacteria for use in the methods and/or compositions of the present invention from a variety of samples. As discussed above, the present inventor also contemplates that new strains of bacteria, for example, recombinant or mutant strains, may be employed in the present invention because, for example, they have improved properties relative to their respective parent strains, for example, they accumulate and/or extrude more ORN or accumulate and/or extrude ORN at a faster rate than the parent strain.

Remarkably, the inventor has found that bacteria with extended "lag" periods are not dead, rather they are dormant and are capable of returning to their reproducing vegetative state. See U.S. Pat. No. 6,589,771 B1. Furthermore, exposing dormant bacteria to environments of neutral pH induces the disassociation of the ORN-DNA complex by reversing the acidification process. The DNA resumes its normal rate of replication and the bacteria return to their vegetative states with normal rates of reproduction. Neutral pH aqueous environments, e.g. saliva, body fluids, physiologic saline, as well as other physiologic fluids, induce bacteria to release accumulated ORNs. See Pending U.S. patent Ser. No. 10/800,926. Extrusion can be induced by subjecting the bacterial populations to repeated dilutions or washings, as many as 6, in pH neutral buffers of sufficient molarity to offset the efflux of $H^+$ that accompany ORN.

The present inventor believes that the presence and release of ORN from bacteria explains their effectiveness in modulating the immune response and providing protection against subsequent endotoxin challenge. See U.S. Pat. No. 5,840,318. The present inventor believes that ORN are the molecular mode of action of probiotics and theorizes that commercially available probiotics are ineffective because they lack ORN. Inventor examined several commercially available probiotics for the presence or absence of ORN. In Example 12, three commercial probiotic products containing *Lactobacilli* were analyzed for their ability to release ORN at a neutral pH into a supernatant. The presence or absence of ORN in the supernatant is determined using a spectrophotometer to measure the absorbance at an ultraviolet (UV) light wavelength of 254 nanometer (nm). Since the UV spectrum of ORNs indicates a maximum at 254 nm, one Arbitrary Unit (AU) of ORN was established as that level of ORN providing an optical density of 0.001 through 1 centimeter (cm) of a solution. See U.S. Pat. No. 5,840,318.

Remarkably, the present inventor has discovered not only a method to increase the level of ORN within a bacterium through ORN accumulation, but also a method for ORN retention in a bacterium. The inventor contemplates that the ability of bacteria to retain and accumulate ORN will be useful in the preparation and administration of compositions for improving the health of humans and animals.

Remarkably, the present inventor has discovered that products containing probiotics lack ORN due to the way the probiotics are produced, including inappropriate pH environments and washing/concentration steps. Although only a few commercially available probiotic products were tested for the presence or absence of ORN, the findings are believed to be representative as most commercial products containing probiotics grow their bacteria in media that is artificially maintained at a neutral pH through the addition of a base. The present invention is based in part on the surprising discovery that allowing the pH of the media to decline during bacterial growth results in the bacterial retention of ORN, and thus the accumulation of the ORN.

In one embodiment, the present invention provides a method for the accumulation of ORN in bacteria. Bacteria are grown in media initially having a neutral pH. Unlike the commercial procedures where the growth media's neutral pH is maintained during the course of natural growth of the bacteria, the present embodiment allows the pH of the media to decline naturally to a pH of from about 6 to about 3.5.

The bacteria are then allowed to spend 1 to 24 hours incubating after entering the stationary phase, preferably from about 10 to 24 hours. Cessation of bacterial growth may be measured using assays using standard techniques known to one skilled in the art, especially the well known assay using the absorbance of the growth media in the visible light range at 540 nm. Increases in the absorbance at 540 nm mirrors the increase of bacterial populations during their log phases. The absorbance stops increasing when bacterial growth stops. The bacteria are then collected, preferably concentrated to a solid wet product in a manner that does not allow the bacteria to be freely suspended in a neutral buffer. Methods for collecting bacteria are well known to one skilled in the art, including centrifugation and filtration. The concentrated bacteria may be washed in a buffer or stored in a suspension having a pH of from about 3.5 to about 6, at a population density of 3 billion cells/mL or less, thereby retaining the accumulated ORNs within the bacteria. The bacteria may be collected using standard techniques, for example centrifugation or a hollow fiber. The bacteria thus produced contain ORNs and the bacteria as such may be prepared for storage or consumption, used for enhancing an animal's immune system, or as a source for ORN for use in compositions to be consumed or to enhance the immune system.

In another embodiment of the present invention, bacteria comprising accumulated ORN may be prepared as described above but the bacteria are collected to a density at or less than 3 billion bacteria per cubic centimeter (cc), thereby further increasing the amount of ORN accumulated. The collected bacteria may be washed in a buffer or stored in a suspension having a pH of from about 3.5 to about 6, preferably from about 3.5 to about 5.5 The bacteria thus produced contain ORNs and the bacteria as such may be prepared for storage or consumption, used for enhancing an animal's immune system, or as a source for ORN for use in compositions to be consumed or to enhance the immune system.

As illustrated in Example 14, bacteria that are concentrated to a density greater than 3 billion cells per cc or mL immediately begin to lose significant amounts of ORN. In other aspects of the invention, if the bacteria are concentrated to a density greater than 3 billion cells per cc and/or washed using a neutral buffer, then a supernatant may be collected and ORN isolated thereof using standard techniques known to one skilled in the art. In another aspect, the ORN are isolated from the supernatant using a hollow fiber tube (J. R. Scientific, Inc. (Woodland, Calif.), used for concentrating bacteria through which the ORN escape. As stated previously, the presence or absence of ORN in the filtrate is determined using a spectrophotometer to measure the absorbance at an ultraviolet (UV) light wavelength of 254 nanometers (nm).

Once the bacteria are collected, they may be washed for 2-5 min using an acidic buffer having a pH of from about 3.5 to about 6; this is in direct contrast to the norm of repeated washing with a pH neutral buffer or solution. Washing with an acidic buffer results in the bacterial retention of ORN, as shown in Example 15. In another aspect of the present invention, the present inventor contemplates that bacteria having accumulated ORN can be freeze-dried and used as a powder for top dressing on animal feed or added to the animals' drinking water or as a gel to be administered directly into the animal's mouth as a supplement. In another aspect, purified ORN can be stored frozen or as a freeze-dried powder.

In one embodiment, the present invention provides a method of preventing the loss of ORN from bacteria during storage, where the method comprises providing bacteria having ORN or accumulated ORN and storing the bacteria having ORN or accumulated ORN in a suspension maintained at a pH of 6 or below using buffers of appropriate strengths. The present inventor contemplates that bacteria containing accumulated ORN may be stored in various suspensions for different lengths of time as desired, provided that the storage suspension has a pH of or less than 6. Suitable methods for storing bacteria are known to one skilled in the art and include, for example, storing the bacteria containing accumulated ORNs for several weeks on agar plates at about 4° C., storing in a glycerol solution at about −20° C. or in a stab agar at about room temperature in a dark environment for about 1-2 years, or storing in glycerol at about −70° C. for a lifetime. See Molecular Cloning, T. Maniatis, E. F. Fritsch, and J. Sambrook. (1982), in particular pages 61-62, 68, 442 and 444. Thus, the present invention provides a method for storing the bacteria having accumulated ORNs at a temperature of from about 4° C. to about −80° C. or below. The present inventor contemplates that the bacteria having accumulated ORN and/or isolated ORN<10 kDa may be freeze-dried and used in powder form.

ORN<10 kDa may be isolated and employed to activate and modulate the immune system of a human or animal as previously described. See U.S. Pat. No. 5,840,318. In another embodiment, bacteria grown under conditions allowing the pH of the media to decline during bacterial growth is exposed to or resuspended in a solution having a neutral or basic pH (e.g. 6-8) to induce the extrusion of ORN from the bacteria. The bacteria are then separated from the solution using methods known to one skilled in the art, including centrifugation and filtration. See U.S. Pat. No. 5,840,318. The presence or absence of ORN in the supernatant or filtrate may be confirmed using a spectrophotometer to measure the absorbance at an ultraviolet (UV) wavelength of 254 nanometers (nm). ORNs<10 kDa may be isolated and purified as previously described. For example, the ORNs<10 kDa may be purified and isolated from a supernatant by filtering the preparation through a 10 kDa filter. The retentate will contain ORN larger than 10 kDa, which the inventor has shown to be non-protective when fed and toxic to mice when injected. The ORN passing through the 10 kDa filter are smaller than 10 kDa and are non-toxic when fed or injected into mice. Further purification is unnecessary for feeding to animals to stimulate the protective immune response. The mixture of ORN<10 kDa can then be chromatographed on a Sephadex G10 column, which further divides the ORN<10 kDa into free bases (adenine and uracil), and mono- to penta-nucleotides. The fractions corresponding to these peaks can be collected and concentrated by rotary evaporation as well as de-ionized.

Disadvantageously, successive steps in commercial production result in the accumulated ORN being lost. These steps include but are not limited to washing the bacteria with neutral buffers and/or concentrating the bacteria in suspension exceeding 3 billion cells per cc. Generally, two types of concentration and washing steps are employed in the production of probiotic bacteria. In the first type, the media containing the suspended bacteria are continuously centrifuged while being spray-washed with water, a saline solution, or a neutral buffer resulting in the pH neutral wash water, solution or buffer carrying away the ORN so that they are lost, most likely down a drain. In the second type of concentration and washing procedure, the media containing the suspended bacteria passes through a hollow fiber having small holes. The holes allow the ORN to escape with the media while the bacteria are being concentrated. Both types of concentration/washing procedures rid the probiotic product of its principle ingredient, the ORN.

Therefore, the present invention of methods has potential applications for optimizing the retention and accumulation of bacterial ORN. Increased yield of ORN will facilitate the production of compositions for activating and modulating the immune system. Techniques for growing, fermenting, and concentrating bacteria are well known to those of ordinary skill in the art and may be used herein.

Additionally, for more information about present inventor's invention, one may reference the book, "The Molecular Naturalist", published by the inventor, which details the reaction by colleagues to the concepts of the invention and the commercial implications of the invention in the age of bioterrorism.

Additional objectives and advantages of the invention are set forth in part in the description, and in part will be obvious from the examples, or may be learned by the practice of the invention. The objectives and advantages of the invention will be obtained by means of the instrumentalities and combinations, particularly pointed out in the claims of the invention.

Although various aspects of the composition are described in detail, it will be apparent to one skilled in the art that modifications, substitutions, and additions may be made without departing from the spirit and scope of the invention. All patents, patent applications, articles and publications mentioned herein, both supra and infra, are hereby incorporated herein by reference. The following examples are described for retention and accumulation of ORN in bacteria or supernatant.

EXAMPLES

The harmless bacteria, *Lactobacillus acidophilus*, *L. caseii*, and *L. plantarum* were grown in MRS broth (Mann-Rogosa-Sharpe). The pathogen, *Listeria monocytogenes* was grown in BHI broth (Brain Heart Infusion). All cultures were grown at 37° C. without shaking into their stationary phases and enumerated by the most probable numbers method of dilution and plating on MRS or BHI agar, respectively.

Broths were microfuged and the pellets suspended in endotoxin-free 0.1M phosphate buffered saline pH 7.3 (PBS). For serial washings of 20 minutes, the PBS was microfuged and the pellet resuspended in PBS for an additional period of 20 minutes.

To remove the bacteria and molecules larger than 10 kDa, the PBS solutions were first passed through a 0.22 mµ filter and then through a filtrate having a cutoff of 10 kDa (Centriplus® 10, Millipore, Medford, Mass.). The retentate holds those ORNs larger than 10 kDa which are not-protective if fed and toxic when injected. The smaller ORNs, those <10 kDa pass through the filter and are found in the filtrate.

The mice were 5-7 week old, female mice (Taconic Farms, N.Y.). The drinking water was autoclaved twice before the bacteria-free preparations of ORNs were added. Forced feeding was via a syringe into the animal's mouth, not stomach.

The endotoxin was derived from *E. coli* 0188:B7 (Sigma St. Louis, Mo.).

Example 1

An i.p. Injection of >200 µg of Endotoxin is Lethal to Mice

Mice were injected with 0.2 mL of endotoxin in phosphate buffered saline and became ill within 2 hr and died within 24 hr. To minimize suffering, moribund mice were sacrificed. The probabilities were determined by the Chi-square test. The same lethality of this endotoxin was found by Beutler B., Milsark I. W., and Cerami A. C., 1985 Passive immunization against cachectin/tumor necrosis factor protects mice from lethal effect of endotoxin. Science 229:869-71.

TABLE 1

| Dose | Alive | Dead | Prob. |
|---|---|---|---|
| 400 µg | 0 | 6 | 0.001 |
| 300 | 0 | 6 | 0.001 |
| 200 | 0 | 6 | 0.001 |
| 100 | 4 | 2 | 0.05 |
| Buffer | 6 | 0 | |

Example 2

The Ad Libitum Consumption of Water Containing Sterile ORNs Protected Mice Against the Lethality of Endotoxin Mice received an i.p. injection of 400 µg of endotoxin after 3 days of consuming water ad libitum, which contained ORN released during a single exposure of individual bacterial cultures to PBS for 16 hr. The mice drank ad libitum approximately 1-2 mL. One mL of the drinking water contained ORN<10 kDa released by $10^9$ CFU of bacteria, about 35 µg.

TABLE 2

| | Alive | Dead | Prob. |
|---|---|---|---|
| *L. monocytogenes* | 7 | 1 | >0.01 |
| Control | 0 | 6 | |
| *L. plantarum* | 4 | 2 | >0.10 |
| Control | 0 | 6 | |
| *L. caseii* | 6 | 16 | 0.20 |
| Control | 0 | 12 | |
| *L. acidophilus* | 6 | 14 | 0.20 |
| Control | 0 | 12 | |

Chi-square test. Controls were PBS.

Example 3

Mice are Protected from Endotoxic Death by a Single Injection of PBS Containing ORN<10 kDa Released by Both Harmless and Pathogenic Bacteria To demonstrate the effectiveness of a single injection of ORN<10 kDa, mice were injected i.p. with 0.2 mL of a sterile preparation of ORN<10 kDa (approximately 7 µg) released during a single 16 hr exposure to PBS by $10^9$ CFU/mL of bacteria followed by a single injection of 400 µg of endotoxin 48 hr later.

Fast-growing feral bacteria have more ribosomes than lab strains and therefore have a greater potential to accumulate ORN. *L. monocytogenes* and *L. plantarum* were feral strains and $10^9$ CFU/mL were more protective than equal populations of the slower growing lab strains of *L. caseii*, *L. acidophilus* and *L. fermentum*.

TABLE 3

| | Alive | Dead | Prob. |
|---|---|---|---|
| *L. monocytogenes* | 9 | 0 | >0.0005 |
| Control | 0 | 9 | |
| *L. plantarum* | 4 | 1 | >0.10 |
| Control | 0 | 5 | |
| *L. caseii* | 2 | 4 | |
| Control | 0 | 6 | |

TABLE 3-continued

|  | Alive | Dead | Prob. |
|---|---|---|---|
| L. acidophilus | 1 | 9 | |
| Control | 0 | 8 | |
| L. fermentum | 0 | 3 | |
| Control | 0 | 3 | |

Example 4

A Dose Response Relationship Exists Between the Amount of ORN<10 kDA Consumed and Protection Against Endotoxic Death Ad libitum consumption of ORN released by a single 16 hr exposure of L. caseii (about 35 µg) afforded more protection than a 10:1 dilution (about 3.5 µg) against the lethality of a subsequent injection of 400 µg of endotoxin.

TABLE 4

|  | Alive | Dead | Prob. |
|---|---|---|---|
| From $1 \times 10^9$ L. caseii | 6 | 6 | >0.20 |
| A 10:1 dilution | 1 | 8 | |
| Control | 0 | 5 | |

Example 5

ORN Larger than 10 kDa are Not Protective

To demonstrate the difference in effectiveness of ORN>10 kDa with those <10 kDA, 0.2 mL of preparations of each released by $10^9$ CFU/mL of L. monocytogenes during a single 16 hr exposure were injected once into mice 48 hr prior to a lethal injection of 400 g of endotoxin.

TABLE 5

|  | Alive | Dead | Prob. |
|---|---|---|---|
| ORN < 10 kDa | 4 | 0 | >0.05 |
| ORN > 10 kDa | 0 | 4 | |
| Control | 0 | 4 | |

Example 6

A single effective feeding dose that protected a 25 g mouse from the lethality of endotoxic shock is approximately 7 µg of ORNs or 280 µg per kg. By extrapolation, a protective dose for an adult human weighing 60 Kg would be about 17 mg of ORN<10 kDa or the level accumulated in 500 cc of yogurt containing $10^9$ CFU/mL of Lactobacilli. To demonstrate the effectiveness of a single forced feeding of ORN<10 kDa, mice were fed 50 µL of sterile ORN released during the first (A), second (B) or third (C) serial washes of 20 min duration each, 48 hr before a lethal injection of 400 µg of endotoxin. The concentration of ORN<10 kDa ranged from a high of in (A).

TABLE 6

|  |  | Alive | Dead | Prob. |
|---|---|---|---|---|
| L. monocytogenes | A | 6 | 3 | >0.20 |
|  | B | 6 | 3 | >0.20 |
|  | C | 0 | 6 | |

TABLE 6-continued

|  |  | Alive | Dead | Prob. |
|---|---|---|---|---|
| Control |  | 0 | 6 | |
| L. plantarum | A | 0 | 3 | >0.15 |
|  | B | 4 | 2 | |
|  | C | 0 | 6 | |
| Control |  | 0 | 4 | |
| L. caseii | A | 1 | 3 | |
|  | B | 0 | 4 | |
|  | C | 0 | 3 | |
| Control |  | 0 | 4 | |

Example 7

ORN Released by Heat-Killed Bacteria Activate Human Monocytes in Cell Culture but do not Protect Mice Against Endotoxic Death To determine the effectiveness of ORN released by heat-killed bacteria, broths containing $10^8$ CFU/mL of L monocytogenes were heated to 100° C. for 40 min. The PBS-ORN were collected from the dead culture after its exposure to PBS for 16 hr. The <10 kDa ORN stimulated monocytes but did not protect mice for a lethal injection of endotoxin. Monocytes at a concentration of 125,000 per well were treated with 10 µL of a 1:1000 dilution of the same preparation of ORN. Probability was determined by the t test.

The test was an adaptation of Mangan D F, Welch G R, Wahl S M. 1991 Lipopolysaccharide, tumor necrosis factor-α, and IL-1B prevent programmed cell death (apoptosis) in human peripheral blood monocytes J Immunol 146:1541-6.

TABLE 7

|  | Mice | | | Monocytes | |
|---|---|---|---|---|---|
|  | Alive | Dead | Prob | Activated | Prob |
| <10 kDa ORN from live bacteria | 4 | 1 | >0.1 | 61% | >0.10 |
| <10 kDa ORN from dead bacteria | 0 | 4 | | 67% | >0.10 |
| Control | 0 | 3 | | 10% | |

Example 8

Mice produced higher levels of IgG against the melanoma antibody MUC-1 when injected three times at one-week intervals with 5 µg of MUC-1 plus 50 µL of sterile ORN<10 kDa released during the first 20 min exposure (A) to PBS, pH 7.3 of L. monocytogenes at $10^9$ CFU/mL. Control was MUC-1 alone.

Pathogen free (Balb/C X C57BL/6) F1 mice, 6 weeks of age were obtained from The Jackson Lab and immunized subcutaneously over the lower abdomen three times at one week intervals with MUC1-KLH and GD3-KLH containing 5 µg of MUC1 and 5 µg of GD3 plus 50 µL of a sterile preparation of ORN<10 kDa. MUC1 is a peptide surface antigen associated with human melanoma cells, which was covalently attached to the immunogenic carrier molecule, keyhole limpet hemocyanin (KLH). A fourth booster immunization was given during week 8. Mice were bled prior to the initial vaccination, 7 days after the third vaccination and 7 days after the fourth vaccination. The ELISA assay was performed as described: MUC1 peptide in 0.1 M carbonate buffer pH 11 was coated on ELISA plates at 0.1-0.2 µg per well. Serially diluted antiserum was added to each well and alkaline phosphatase-conjugated goat anti-mouse IgG or anti-mouse IgM was added at a dilution of 1:200 (Southern Biotech Assoc, Inc., Birmingham, Ala.). ELISA titer is defined as the highest dilution yielding an absorbance of 0.1 or greater over that of normal mouse control sera.

TABLE 8

| | Reciprocal of Titer | |
|---|---|---|
| Week | Control Animals | Treated Animals |
| 1 | 580 | 1280 |
| 2 | 1780 | 12320 |
| 3 | 1780 | 4840 |
| 7 | 1040 | 4800 |
| 8 | 1780 | 6800 |

Example 9

Bacteria became hypermutative after 6 serial washes in PBS. On agar the hypermutative population presented polymorphic morphologies and in the disk assay, increased susceptibility to Kanamycin® and Polymixin B®.

The disk diffusion assay was used to determine the susceptibility of vegetative forms of *L. monocytogenes*, before and after 6 serial 20-min washes in PBS. (See Bauer, A, Kirby, W, Sherris, J, Turck, M, 1966 Antibiotic Susceptibility Testing by a Standardize Single Disk Method, Amer J Clin Path 36:41-44).

TABLE 9

| | Diameter of Zone of Inhibition | |
|---|---|---|
| Antimicrobial | Before Washing | After 6 Washes |
| Ampicillin, 10 µg | 32 mm (3.8) | 30 mm (3.6) |
| Kanamycin, 30 µg | 11 (2.66) | 18* (1.97) |
| Polymixin B, 300 IU | 0 | 11** (3.25) |
| Tetracycline, 30 µg | 40 (5.0) | 45 (6.3) |
| Vancomycin, 30 µg | 25 (3.7) | 30 (4.2) |

Data are averages of 6 experiments. SD is in parentheses. Data marked with asterisks are significantly different from corresponding data. **P>0.0025 as determined by the t test for comparing 2 means.

Example 10

Figure 2:
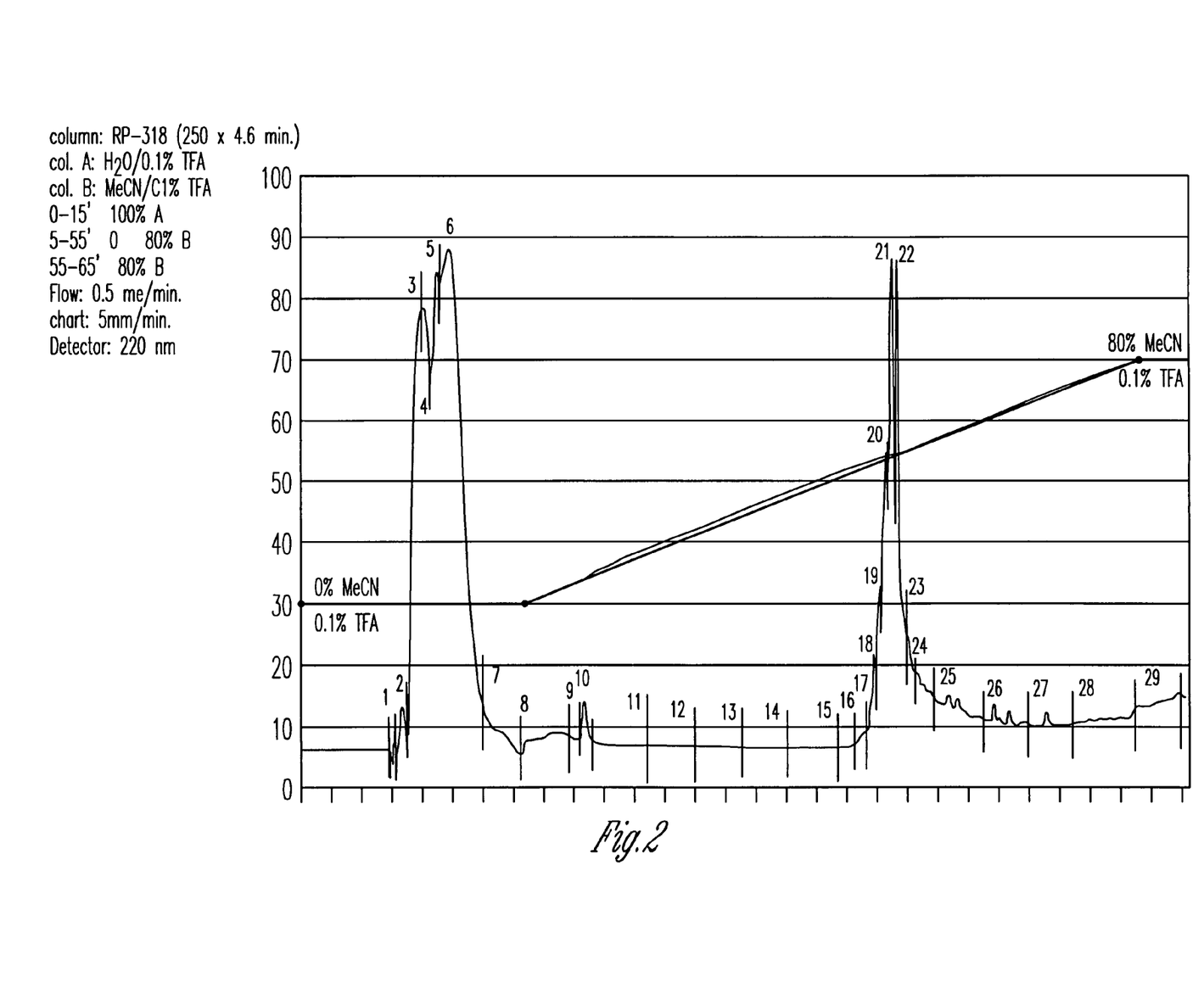

High Pressure Liquid Chromatography (HPLC) of ORNs <10 kDa Reference FIG. 2

FIG. 2 displays a chromatogram of the separation of the ORN<10 kDa released over a 12 hr period by *L. monocytogenes*. It shows 7 major components, 4 hydrophilic and 3 hydrophobic.

The column was 250 mm×4.6 mm and packed with RP 315 by the manufacturer, BioRad. The first solvent used was aqueous, 0.1% trifluoro-acetic acid, which eluted the group of hydrophilic ORN between 7 and 11 min. A second solvent was then applied to elute the group of hydrophobic ORNs. It was a progressive solvent beginning with 0% Methyl Cyanide and 0.1% trifluoro-acetic acid and ending after 55 min with 80% Methyl Cyanide and 0.1% trifluoro-acetic acid.

The hydrophilic group consists of 4 major components (labeled "3, 4, 5, and 6") and eluted between 7 and 11 min by 0.1% trifluoro-acetic acid in water. The hydrophobic group consists of 3 major components (labeled "20, 21, and 22") eluted between 38 and 40 min by an aqueous solvent of about 48% Methyl Cyanide and 0.1% trifluoro-acetic acid. Numerous smaller peaks can be observed in the tracing.

The detector was absorbance at 220 nm. Aliquots of both hydrophilic and hydrophobic groups showed UV maxima at 254 nm.

Example 11

Figure 1:
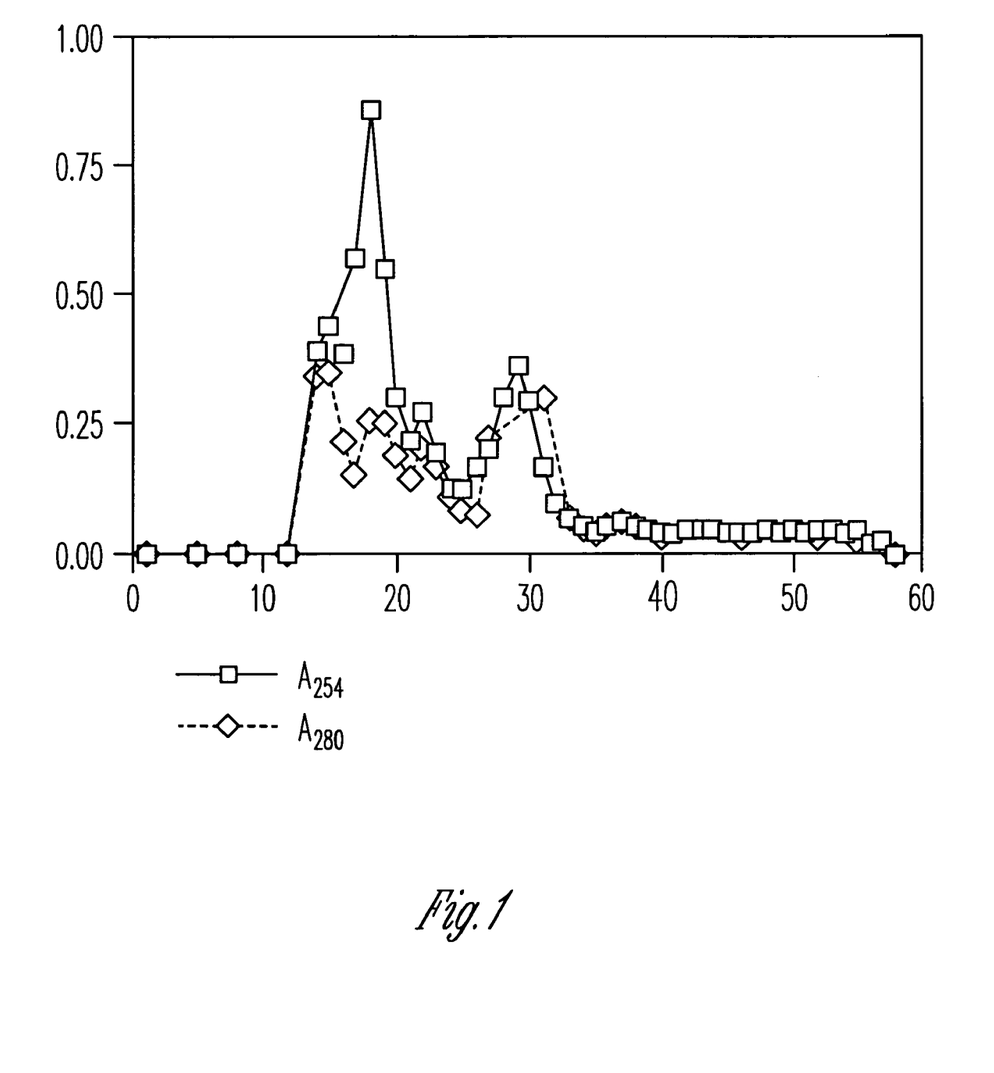
FIG. 1 illustrates the distribution of the molecular sizes of the ORN<10 kDa released by exposing harmless or pathogenic bacteria to 0.1M phosphate buffered saline, pH 7.3 on a Sephadex G-10 column. Since the average molecular weight of a monoribonucleotide is about 309 Da or 0.3 kDa, a mixture of ORNs<10 kDa may contain oligonucleotides containing as many as 33 mononucleotides. Slightly less than half of the ORN eluted at the void volume (Peak I) indicating sizes >1. kDa.

Standards and fractions collected from chromatography on Sephadex G-10 of ORN<10 kDa released by *L. monocytogenes* as shown in FIG. 1 were analyzed by thin layer chromatography. From standards of adenine, cytosine, guanine and uracil chromatographed on Sephadex G-10 and on thin layer chromatography (shown below), Peak III was judged to be free uracil and adenine. Peak I contains the mixture of approximately 6 hydrophobic ORN. Peak II contains ORNs that are approximately 3-5 nucleotides. Peak IV contains ORN that are mono and dinucleotides. Free thymine was not found suggesting the absence of products of hydrolyzed DNA, which was expected since washing in PBS did not result in a significant number of deaths in the bacterial population.

$R_f$ values are the quotient of the distance that a substance migrates divided by the distance traveled by the solvent. Their values are determined by the relative solubilities in the solvents used. In general, the larger oligonucleotides are less soluble and have corresponding lower $R_f$ values.

TABLE 10

| | $R_F$ Values | |
|---|---|---|
| Plates pre-coated with: | Silica | Cellulose |
| Peak I | 0.0-0.1 | 0-.23 |
| Peak II | .44 | |
| Peak III | .58 | .58 |
| Peak IV | .47 | |
| Adenine | | .23 |
| Cytosine | .57 | .35 |
| Guanine | .62 | .13 |
| Thymine | .62 | .72 |
| Uracil | .60 | .60 |
| Adenosine | .80 | .26 |
| Cytidine | .58 | .34 |
| Guanosine | .59 | .225 |
| Thymidine | | .69 |
| Uridine | .58 | .57 |
| AMP | .15 | |
| CAMP | .62 | |
| CMP | .09 | |
| GMP | .07 | |
| UMP | .07 | |
| UTP | .05 | |
| TTP | .141 | |

The solvent used to develop the ORN<10 kDa on pre-coated silica G-25 plates (EM Science) was 2-propanol:concentrated ammonium:water (6:3:1) as recommended by Scheit, K-H., 1967; Silacagel-Dunnschichtchromatographie von Nucleosiden, Nucleotiden und Oligonucleotiden Biochim., Biophys. Acta 134:217-20. The solvent migrated 8-10 cm up the plate over 2 hrs. After drying it was viewed under a UV lamp emitting rays at 254 nm; a duplicate plate was charred with sulfuric acid to expose all compounds. The spots observed under the UV lamp corresponded to those seen by charring.

The solvent to develop the ORN<10 kDa on pre-coated cellulose plates (EM Science) was isopropanol:concentrated hydrochoric acid:water (65:16.7:18.3) recommended by Grippo, P., M. Iaccarino, M. Rossi, and E. Scarano 1965; Thin-layer chromatography of nucleotides, nucleosides and nucleic acid bases. Biochim. Biophys. Acta 65:95: 1-7. The solvent migrated 8-10 cm up the plate over 2 hr. After drying the plate was viewed under a short wave UV lamp at 254 nm, and a duplicate plate charred with sulfuric acid to expose spots of organic nature. The spots absorbing the UV light were the only ones seen by charring.

Example 12

Bacteria Do Not Retain ORN when Grown Under Regulated pH

Three commercial probiotic products containing *Lactobacilli* were obtained and analyzed: A, B and C. Each had been grown under regulated conditions, holding the pH constant at 7. One hundred mg of commercial product were suspended with gentle shaking in 10 mL of 0.1M PBS for 20 min. The bacterial pellet was collected by centrifugation and again suspended in fresh 0.1M PBS for 20 min. Supernatant from the second centrifugation was passed through a 0.22 μm filter to remove traces of bacteria. The supernatants did not demonstrate a peak at 254 nm, indicating that ORN were not released.

|  | Absorbance | | |
| --- | --- | --- | --- |
| UV Wavelength | Product A | Product B | Product C |
| 220 nm | 16.4 | 19. | 23. |
| 240 | 5.4 | 16. | 11. |
| 254 | 6.8 | 15. | 6.2 |
| 260 | 7.6 | 15.5 | 5.9 |
| 270 | 8.0 | 16.4 | 6. |
| 280 | 8.4 | 17. | 6.15 |

Example 13

Bacteria Retain ORN when Grown Under Unregulated pH

*Lactobacilli* were grown in de Mann-Rogosa-Sharpe (MRS) media, at a starting pH of 7.3, into stationary phase. Without regulating the pH it slowly decreased reaching a steady condition of pH 5.5 after about 24 hr. The bacterial pellet was collected by centrifugation and suspended in 0.1M phosphate buffered saline (PBS) for 20 min. The bacterial pellet was again recovered by centrifugation and re-suspended in PBS for a second period of 20 min. The suspension was centrifuged and the supernatant passed through a 0.22 μm filter to remove any traces of bacteria. The supernatant had a peak of absorbance at 254 nm coinciding with the peak absorbance of ORN.

| UV Wavelength | Absorbance | Arbitrary Units of ORNs |
| --- | --- | --- |
| 220 nm | 5.6 | |
| 240 | 4.7 | |
| 254 | 7.2 | 7200. AU |
| 260 | 7.2 | |
| 270 | 5.0 | |
| 280 | 3.7 | |

Example 14

Bacteria Lose ORN if Concentrated to Densities >3 Billion Per cc

*Lactobacilli* were grown in MRS media, at a starting pH of 7.3, into stationary phase. Without regulating the pH, the pH slowly decreased reaching a steady condition of pH 5.5 after about 24 hr. The broth was transferred into a hollow fiber for concentration. Liquid and substances smaller than the bacteria, including ORNs, passed through holes in the fiber, concentrating the bacteria to 10 billion per cc.

The filtrate showed that the ORN were released by the bacteria at these high populations and passed into the filtrate. The filtrate had a peak absorbance of 15.7 at 254 nm indicating the presence of ORN. (See Column 1, "Filtrate").

The retentate, containing the concentrated bacteria at a population density of 10 billion cells/mL, was suspended in 0.1M PBS for 20 min, filtered to remove the bacteria and the filtrate examined in the UV. The absence of a peak at 254 nm (12) indicates that the ORN were not retained in the bacteria at a population density of 10 billion/mL. (See Column 2).

|  | Absorbance at UV Wavelengths | |
| --- | --- | --- |
| Wavelength | Filtrate | Released by Bacteria |
| 220 | 23 | 26. |
| 240 | 16.6 | 17. |
| 254 | 15.7 | 12. |
| 260 | 15.5 | 12.5 |
| 280 | 12.2 | 14.5 |
| 290 | 11.5 | |

Example 15

Bacteria Retain ORN if Washed in Buffers of Acidic pH

*L. caseii* was grown in MRS media from a starting pH of 7.3 into stationary phase without regulating the pH. The pellet was collected by centrifugation and washed for two 20 min periods in 0.1M buffers of various pH values. A bacteria-free preparation was made by filtering through a 0.22 mμ filter and examined in the UV at 254 nm.

|  | Absorbance of Filtrate at 254 nm | |
| --- | --- | --- |
| pH of buffer | 1st Washing | 2nd Washing |
| 3.3 | 1.976 | 2.435 |
| 4.0 | 2.466 | 2.995 |
| 4.6 | 2.987 | 8.030 |
| 5.0 | 4.58 | 14.95 |
| 5.6 | 7.29 | 17.63 |
| 5.7 (0.1 M phosphate) | 6.98 | 18.58 |
| 7.65 (0.1 M phosphate) | 12.80 | 12.88 |
| 7.0 (saline, no buffer) | 6.16 | 15.88 |

*L. caseii* and *L. monocytogenes* were washed for 20 min in buffers over a range of pH values. The preparation was filtered to remove bacteria and the filtrate examined at 254 nm.

|  | UV Analyses | |
| --- | --- | --- |
|  | Absorbance of Filtrate at 254 nm | |
| pH of buffer | *L. caseii* | *L. monocytogenes* |
| 4.0 | 2.92 | 7.54 |
| 7.2 | 22.80. | 20.60. |

What is claimed is:

1. A method of producing bacteria comprising immune-enhancing, bacterial-derived ribonucleotides (ORN) for supplementing animal feed or drinking water comprising:
   growing bacteria in a medium wherein the initial pH of said medium has a neutral pH;
   allowing the bacteria to acidify the medium so that said ribonucleotides are produced and accumulated within said bacteria;
   allowing the bacteria to enter their stationary phase wherein the viable bacteria have ceased to increase;
   collecting the bacteria under acid pH conditions to minimize release of said ribonucleotides; and
   washing said collected bacteria using a buffer having a pH of from about 3.5 to less than or equal to 6.

2. The method of claim 1 wherein the bacteria are of a genera selected from the group consisting of *Lactobacillus, Bifidobacterium, Staphylococcus, Streptococcus, Pseudomonas, Propionibacterium, Bacillus, Escherichia, Enterococcus*, and mixtures thereof.

3. The method of claim 1 further comprising incubating the bacteria 1 to 24 hours after entry into said stationary phase.

4. The method of claim 1, wherein the collected bacteria are concentrated to a density of less than 3 billion bacteria per mL.

5. The method of claim 1 further comprising collecting the bacteria using centrifugation or a hollow fiber at a pH of 6 or less.

6. The method of claim 1 further comprising freeze drying or gelling the collected bacteria.

* * * * *

```
                              SEQUENCE LISTING

<160> NUMBER OF SEQ ID NOS: 2

<210> SEQ ID NO 1
<211> LENGTH: 10
<212> TYPE: DNA
<213> ORGANISM: Escherichia coli

<400> SEQUENCE: 1
ggttatacac                                                              10

<210> SEQ ID NO 2
<211> LENGTH: 10
<212> TYPE: DNA
<213> ORGANISM: Escherichia coli

<400> SEQUENCE: 2
gtgtataacc                                                              10
```